United States Patent
Johnson et al.

(10) Patent No.: US 9,216,938 B2
(45) Date of Patent: Dec. 22, 2015

(54) PROCESS FOR THE PRODUCTION OF (METH)ACRYLIC ACID AND DERIVATIVES AND POLYERS PRODUCED THEREFROM

(75) Inventors: David William Johnson, Durham (GB); Graham Ronald Eastham, Durham (GB); Martyn Poliakoff, Nottingham (GB); Thomas Andrew Huddle, Guildford (GB)

(73) Assignee: Lucite International UK Limited, Hampshire (GB)

( * ) Notice: Subject to any disclaimer, the term of this patent is extended or adjusted under 35 U.S.C. 154(b) by 0 days.

(21) Appl. No.: 13/984,473

(22) PCT Filed: Feb. 8, 2012

(86) PCT No.: PCT/GB2012/050272
§ 371 (c)(1),
(2), (4) Date: Oct. 16, 2013

(87) PCT Pub. No.: WO2012/107758
PCT Pub. Date: Aug. 16, 2012

(65) Prior Publication Data
US 2014/0031501 A1  Jan. 30, 2014

(30) Foreign Application Priority Data

Feb. 9, 2011 (GB) .................................. 1102249.8
Jun. 24, 2011 (GB) .................................. 1110741.4

(51) Int. Cl.
| | |
|---|---|
| C07C 67/08 | (2006.01) |
| C07C 51/48 | (2006.01) |
| C07C 51/38 | (2006.01) |
| C08F 20/06 | (2006.01) |
| C08F 20/02 | (2006.01) |

(52) U.S. Cl.
CPC .................. *C07C 51/48* (2013.01); *C07C 51/38* (2013.01); *C08F 20/02* (2013.01); *C08F 20/06* (2013.01)

(58) Field of Classification Search
CPC .......... C07C 51/48; C07C 51/38; C07C 57/04
USPC ........................................ 562/598, 599, 600
See application file for complete search history.

(56) References Cited

U.S. PATENT DOCUMENTS

| | | | |
|---|---|---|---|
| 2,504,049 A | | 4/1950 | Richards |
| 3,962,074 A | | 6/1976 | Schropp |
| 3,968,153 A | | 7/1976 | Ohrui et al. |
| 4,142,058 A | | 2/1979 | Matsumura et al. |
| 4,555,557 A | * | 11/1985 | Fukumoto et al. ............ 526/240 |
| 4,879,412 A | | 11/1989 | Iwasaki et al. |
| 4,956,493 A | | 9/1990 | Ueoka et al. |
| 5,196,578 A | | 3/1993 | Kuragano et al. |
| 5,612,417 A | | 3/1997 | Rhein et al. |
| 2005/0085607 A1 | | 4/2005 | Kabs et al. |
| 2010/0273970 A1 | | 10/2010 | Koestner et al. |
| 2011/0287991 A1 | | 11/2011 | Dubois |
| 2012/0309911 A1 | | 12/2012 | Johnson et al. |
| 2013/0303713 A1 | | 11/2013 | Johnson et al. |

FOREIGN PATENT DOCUMENTS

| | | |
|---|---|---|
| BE | 550 710 A | 12/1959 |
| CN | 101497563 A | 8/2009 |
| EP | 0710643 | 5/1996 |
| EP | 0 716 122 A2 | 6/1996 |
| JP | H08-208917 A | 8/1996 |
| JP | 2005-516089 A | 6/2005 |
| JP | 2013-515046 A | 5/2013 |
| JP | 2014-505668 A | 3/2014 |
| WO | WO-9619434 | 6/1996 |
| WO | WO-2010/058119 A1 | 5/2010 |
| WO | WO-2011077140 A2 | 6/2011 |

OTHER PUBLICATIONS

Carlsson et al. (Study of the Sequential Conversion of Citric to Itaconic to Methacrylic Acid in Near-Critical and Supercritical Water, Ind. Eng. Chem. Res. vol. 33, 1989-1996, 1994).*
Office Action issued in New Zealand Patent Application No. 613224 dated May 5, 2014.
International Search Report in PCT International Application No. PCT/GB2012/050272 dated May 7, 2012.
Magnus et al., "Study of the sequential conversion of citric to itaconic to methacrylic acid in near-critical and supercritical water," Industrial & Engineering Chemistry Research, American Chemical Society, vol. 33, No. 8, pp. 1989-1996 (1994).
International Preliminary Report on Patentability issued in International Application No. PCT/GB2012/050272 dated Aug. 13, 2013.
Carlsson et al., "Study of the sequential conversion of citric to itaconic to methacrylic acid in near-critical and supercritical water," Industrial & Engineering Chemistry Research, American Chemical Society, vol. 33, No. 8, pp. 1989-1996 (1994).

(Continued)

*Primary Examiner* — Yevegeny Valenrod
*Assistant Examiner* — Blaine G Doletski
(74) *Attorney, Agent, or Firm* — Venable LLP; Keith G. Haddaway; Annette K. Kwok

(57) ABSTRACT

A method of extracting (meth)acrylic acid from an aqueous reaction medium into an organic phase in contact therewith is described. The aqueous reaction medium is formed from at least one base catalyst and at least one dicarboxylic acid selected from maleic, fumaric, malic, itaconic, citraconic, mesaconic, and citramalic acid or mixtures thereof in aqueous solution and contains the base catalysed decarboxylation products of the base catalysed reaction. The method includes either the addition of at least one of the said dicarboxylic acids and/or a pre-cursor thereof to the aqueous reaction medium to enhance the solvent extraction of the (meth)acrylic acid into the organic solvent or maintaining the level of base catalyst to dicarboxylic acid and/or pre-cursor at a sub-stoichiometric level during the extraction process. The method extends to a process of producing (meth)acrylic acid, its esters and polymers and copolymers thereof.

18 Claims, 6 Drawing Sheets

(56) References Cited

OTHER PUBLICATIONS

Communication pursuant to Rules 161(1) and 162 EPC in European Patent Application No. 11791623.9-1451, dated Jul. 2, 2013.
International Preliminary Report on Patentability and Written Opinion in PCT International Application No. PCT/GB2011/052271, dated May 28, 2013.
International Search Report in PCT International Application No. PCT/GB2011/052271 dated Feb. 7, 2012.
Li et al., Spectroscopy of Hydrothermal Solutions 18: pH-Dependent Kinetics of Itaconic Acid Reactions in Real Time, Journal of Physical chemistry A vol. 105, pp. 10839-10845, 2001.
Office Action issued in Chinese Patent Application No. 201180056814.1 dated May 27, 2014.
Office Action issued in U.S. Appl. No. 13/989,363 dated Oct. 24, 2014.
Salov et al., High-Temperature conversions of alkyl-substituted acrylic acids in aqueous, Zhurnal Organicheskoi Khimii, vol. 19, No. 10, pp. 2052-2054, 1983 (abstract accession No. 1984:22312).
Search Report in Application No: GB1019915.6 dated May 18, 2011.
Office Action issued in U.S. Appl. No. 13/989,363 dated Mar. 18, 2015.
Notice of Allowance issued in U.S. Appl. No. 13/989,363 dated Jun. 29, 2015.

* cited by examiner

PROCESS FOR THE PRODUCTION OF (METH)ACRYLIC ACID AND DERIVATIVES AND POLYERS PRODUCED THEREFROM

The present invention relates to a process for the production of (meth)acrylic acid (meaning herein acrylic acid or methacrylic acid) or derivatives such as esters thereof by the decarboxylation of selected acids in the presence of base catalysts and the extraction of the (meth)acrylic acid product from the reaction medium.

Acrylic acid (AA) and Methacrylic acid (MAA) and their esters, particularly methyl, ethyl and butyl esters, such as ethyl acrylate, butyl acrylate, methyl methacrylate (MMA) and butyl methacrylate are important monomers in the chemical industry. Their main application is in the production of polymers for various applications. The most significant polymer applications are for acrylic acid in superabsorbent polymers, and methacrylate and acrylate esters for surface coatings and for high optical clarity plastics produced by the casting, moulding or extrusion of polymethyl methacrylate (PMMA). In addition, many copolymers of AA and its esters and MAA or MMA are used; important copolymers are copolymers of MMA with α-methyl styrene, ethyl acrylate and butyl acrylate. Currently AA, MMA and MAA are produced entirely from petrochemical feedstocks.

Conventionally, MMA has been produced industrially via the so-called acetone-cyanohydrin route. The process is capital intensive and produces MMA from acetone and hydrogen cyanide at a relatively high cost. The process is effected by forming acetone cyanohydrin from the acetone and hydrogen cyanide: dehydration of this intermediate yields methacrylamide sulphate, which is then hydrolysed to produce MAA. The intermediate cyanohydrin is converted with sulphuric acid to a sulphate ester of the methacrylamide, methanolysis of which gives ammonium bisulphate and MMA. However, this method is not only expensive, but both sulphuric acid and hydrogen cyanide require careful and expensive handling to maintain a safe operation and the process produces large amounts of ammonium sulphate as a by-product. Conversion of this ammonium sulphate either to a useable fertilizer or back to sulphuric acid requires high capital cost equipment and significant energy costs.

Alternatively, in a further process, it is known to start with an isobutylene or, equivalently, t-butanol reactant which is then oxidized to methacrolein and then to MAA.

An improved process that gives a high yield and selectivity and far fewer by-products is a two stage process known as the Alpha process. Stage I is described in WO96/19434 and relates to the use of 1,2-bis-(di-t-butylphosphinomethyl)benzene ligand in the palladium catalysed carbonylation of ethylene to methyl propionate in high yield and selectivity. The applicant has also developed a process for the catalytic conversion of methyl propionate (MEP) to MMA using formaldehyde. A suitable catalyst for this is a caesium catalyst on a support, for instance, silica. This two stage process although significantly advantageous over the competitive processes available still nevertheless relies on ethylene feed stocks predominantly from crude oil and natural gas, albeit bioethanol is also available as a source of ethylene.

Acrylic acid is conventionally prepared by oxidation of propene which is derived exclusively from oil, gas or coal feedstocks.

For many years, biomass has been offered as an alternative to fossil fuels both as a potential alternative energy resource and as an alternative resource for chemical process feedstocks. Accordingly, one obvious solution to the reliance on fossil fuels is to carry out any of the known processes for the production of AA, MMA or MAA using a biomass derived feedstock.

In this regard, it is well known that syngas (carbon monoxide and hydrogen) can be derived from Biomass and that methanol can be made from syngas. Several Industrial plants produce methanol from syngas on this basis, for example, at Lausitzer Analytik GmbH Laboratorium für Umwelt and Brennstoffe Schwarze Pumpe in Germany and Biomethanol Chemie Holdings, Delfzijl, Netherlands. Nouri and Tillman, Evaluating synthesis gas based biomass to plastics (BTP) technologies, (ESA-Report 2005:8 ISSN 1404-8167) teach the viability of using methanol produced from synthesis gas as a direct feedstock or for the production of other feedstocks such as formaldehyde. There are also many patent and non-patent publications on production of syngas suitable for production of chemicals from biomass.

The production of ethylene by dehydration of biomass derived ethanol is also well established with manufacturing plants in, especially, Brazil.

The production of propionic acid from carbonylation of ethanol and the conversion of biomass derived glycerol to molecules such as acrolein and acrylic acid is also well established in the patent literature.

Thus ethylene, carbon monoxide and methanol have well established manufacturing routes from biomass. The chemicals produced by this process are either sold to the same specification as oil/gas derived materials, or are used in processes where the same purity is required.

Thus in principle there is no barrier to operation of the so called Alpha process above to produce methyl propionate from Biomass derived feedstocks. In fact, its use of simple feedstocks such as ethylene, carbon monoxide and methanol rather sets it apart as an ideal candidate.

In this regard, WO2010/058119 relates explicitly to the use of biomass feedstocks for the above Alpha process and the catalytic conversion of methyl propionate (MEP) produced to MMA using formaldehyde. These MEP and formaldehyde feedstocks could come from a biomass source as mentioned above. However, such a solution still involves considerable processing and purification of the biomass resource to obtain the feedstock which processing steps themselves involve the considerable use of fossil fuels.

Further, the Alpha process requires multiple feedstocks in one location which can lead to availability issues. It would therefore be advantageous if any biochemical route avoided multiple feedstocks or lowered the number of feedstocks.

Acrylic acid is conventionally prepared by oxidation of propene which is derived exclusively from oil, gas or coal feedstocks.

Therefore, an improved alternative non-fossil fuel based route to acrylate monomers such as AA, MMA and MAA is still required.

PCT/GB2010/052176 discloses a process for the manufacture of aqueous solutions of acrylates and methacrylates respectively from solutions of malic and citramalic acids and their salts.

Carlsson et al. Ind. Eng. Chem. Res. 1994, 33, 1989-1996 has disclosed itaconic acid decarboxylation to MAA at high temperatures of 360° C. and with a maximum yield of 70% where a proportion of the acid is present as a base salt, for instance, sodium itaconate. Unfortunately, Carlsson does not disclose any purification methodology to recover the MAA from the reaction medium. Carlsson discloses that the activity for the decomposition reaction increases with the concentration of the sodium salt relative to the free acid. The selectivity falls as the concentration of itaconic acid is raised in the solution prior to decomposition.

U.S. Pat. No. 4,142,058 discloses the extraction of methacrylic acid from acidic aqueous solutions using mixtures of MMA and toluene under counter current flow. The aqueous phase goes to waste. U.S. Pat. No. 3,968,153 discloses the extraction of acrylic and/or methacrylic acid from an aqueous phase using methylethyl ketone and xylenes. U.S. Pat. No. 4,956,493 discloses extracting methacrylic acid from its aqueous solution using a saturated chain aliphatic hydrocarbon having 6 to 9 carbon atoms as a solvent. Xylene and toluene are said to be problematic. EP 710643 uses an organic solvent to extract methacrylic acid from its aqueous solution and treats the organic extract with water to assist in the removal of close boiling acids citraconic and maleic acid from the extract. U.S. Pat. No. 4,879,412 and JP 193740/1989 discuss the treatment of the organic phase with a basic ion exchange resin and U.S. Pat. No. 5,196,578 discloses a similar process using amines. The processes are problematic because they introduce additional impurities and can lead to by-products that cause polymerisation of the methacrylic acid leading to equipment failure.

Those skilled in the art would realise that the conditions of the solution generated according to the teaching of Carlsson et al would not be suitable for subsequent solvent extraction because of the low concentration of MAA and the high concentration of base. Basic salts of AA and MAA have high solubilities in water and very low solubilities in organic solvents.

Surprisingly, it has now been discovered that AA and MAA can be extracted from an aqueous decarboxylation reaction medium in the presence of a basic catalyst with a surprisingly improved yield. Furthermore, the extraction process allows the basic solutions after extraction to be recycled into the decarboxylation reaction so that a continuous decarboxylation and extraction process to generate AA and MAA from di and tri carboxylic acids can be achieved with a single addition of base, such that the base catalysed reaction may be conducted continuously.

According to a first aspect of the present invention there is provided a method of extracting (meth)acrylic acid from an aqueous reaction medium, the aqueous reaction medium being formed from at least one base catalyst and at least one dicarboxylic acid selected from maleic, fumaric, malic, itaconic, citraconic, mesaconic and citramalic acid or mixtures thereof in aqueous solution and containing the base catalysed decarboxylation products thereof including (meth)acrylic acid and/or (meth)acrylate base salt, the method comprising the steps of introducing an organic solvent to the said aqueous reaction medium for solvent extraction of the (meth)acrylic acid into an organic phase wherein the method is characterised in that there is added an additional amount of at least one of the said dicarboxylic acids and/or a pre-cursor thereof to the said aqueous reaction medium to enhance the solvent extraction of the (meth)acrylic acid into the organic solvent.

Preferably, the concentration of (meth)acrylic acid in the aqueous phase extraction is at least 0.05 mol dm$^{-3}$, more preferably, at least 0.1 mol dm$^{-3}$, most preferably, at least 0.2 mol dm$^{-3}$, especially, at least 0.3 or 0.4 mol dm$^{-3}$. In a batch reaction, this concentration applies to the reaction medium at the start of the extraction and in a continuous process applies to the starting point in the extraction. The concentration of (meth)acrylic acid at the end of the extraction will depend on the number of stages but will preferably be below 50%, more preferably 30%, most preferably 20% of the starting level.

Advantageously, concentrations of the (meth)acrylic acid at these levels result in better extraction into the organic phase.

Generally, the base catalyst molar concentration in the aqueous reaction medium during the extraction of (meth)acrylic acid therefrom is ≤the overall acid concentration therein mol/mol, more preferably, the base catalyst molar concentration ≤75% mol/mol of the overall acid concentration during the extraction, most preferably, the base catalyst molar concentration in the aqueous reaction medium during the extraction of (meth)acrylic acid therefrom is ≤the non (meth)acrylic acid acid concentration mol/mol, more especially, ≤80% of the non (meth)acrylic acid acid concentration mol/mol during the extraction.

Preferably, the molar level of base catalyst to the said at least one dicarboxylic acid and/or pre-cursor thereof is maintained at a sub-stoichiometric level in relation to the formation of the first acid salt thereof during the extraction process and the amount of dicarboxylic acid added is determined accordingly.

Suitable mixtures of dicarboxylic acid for the production of methacrylic acid are itaconic, citramalic, citraconic and mesaconic acid, more preferably, itaconic, citramalic and citraconic acid. Suitable mixtures of dicarboxylic acid for the production of acrylic acid are maleic, fumaric, and malic acid, more preferably, malic acid.

Advantageously, the extraction does not require addition of any process external agents to the aqueous phase so that the aqueous phase can easily and efficiently be recycled into the decarboxylation reaction medium for further decarboxylation under base catalysed conditions followed by further extraction. In this way no or little additional base is required to process further dicarboxylic acid to (meth)acrylic acid. Equally the only acids added to the system are those dicarboxylic acids and/or pre-cursor acids involved in the production of (meth)acrylic acid or those acids formed in the production process. No external inorganic acid is required.

According to a second aspect of the present invention there is provided a method of extracting (meth)acrylic acid from an aqueous reaction medium, the aqueous reaction medium being formed from at least one base catalyst and at least one dicarboxylic acid selected from fumaric, maleic, malic, itaconic, citraconic, mesaconic or citramalic acid or mixtures thereof in aqueous solution and containing the base catalysed decarboxylation products thereof including (meth)acrylic acid or (meth)acrylate base salt, the method comprising the steps of introducing an organic solvent to the aqueous reaction medium for solvent extraction of the (meth)acrylic acid into the organic phase characterised in that the level of base catalyst to the said at least one dicarboxylic acid and/or pre-cursor thereof is maintained at a sub-stoichiometric level in relation to the formation of the first acid salt thereof during the extraction process.

According to a further aspect of the present invention there is provided a method of extracting (meth)acrylic acid from an aqueous reaction medium into an organic phase in contact therewith, the aqueous reaction medium being formed from at least one base catalyst and at least one dicarboxylic acid selected from fumaric, maleic, malic, itaconic, citraconic, mesaconic or citramalic acid or mixtures thereof in aqueous solution and containing the base catalysed decarboxylation products thereof including (meth)acrylic acid or (meth)acrylate base salt and the organic phase comprises a suitable organic solvent for the said (meth)acrylic acid characterised in that in the aqueous reaction medium the relative level of base catalyst to the said at least one dicarboxylic acid and/or pre-cursor thereof is maintained at a sub-stoichiometric level in relation to the formation of the first acid salt thereof during at least part of the extraction.

According to a still further aspect of the present invention there is provided a method of extracting (meth)acrylic acid from an aqueous reaction medium, the aqueous reaction medium being formed from at least one base catalyst and at least one dicarboxylic acid selected from maleic, fumaric, malic, itaconic, citraconic, mesaconic or citramalic acid or mixtures thereof in aqueous solution and containing the base catalysed decarboxylation products thereof including (meth)acrylic acid and/or (meth)acrylate base salt, the method comprising the step of solvent extraction of the (meth)acrylic acid into an organic phase comprising an organic solvent in contact with the said aqueous reaction medium wherein the method is characterised in that there is added an additional amount of at least one of the said dicarboxylic acids and/or a pre-cursor thereof to the said aqueous reaction medium containing the said base catalysed decarboxylation products thereof to enhance the solvent extraction of the (meth)acrylic acid into the organic phase.

Preferably, the method of any aspect herein includes the step of separating the organic phase from the aqueous phase after extraction followed by subsequent treatment of the organic phase to isolate the (meth)acrylic acid extracted in the extraction process from the organic solvent. A suitable treatment of the organic phase is distillation to obtain the (meth)acrylic acid.

It will be understood that the dicarboxylic acid being a dibasic acid can form a first and second acid salt thereof with a base and the term first acid salt should be understood accordingly and is not intended to refer to the salt with a second or further acid group on the dicarboxylic acid or pre-cursor thereof but only the first acid salt that forms.

Advantageously, by maintaining the base at sub-stoichiometric first acid salt levels with respect to the level of dicarboxylic acid and/or pre-cursor in the aqueous medium/reaction medium the extraction of the (meth)acrylic acid into the suitable organic solvent is improved.

Preferably, in the case of decomposition of acids for the formation of MAA, the organic solvent is an external organic solvent with respect to the aqueous medium/reaction medium.

Preferably, at least some citraconic acid is present in the aqueous medium. Advantageously, this improves the extraction. However, the most suitable acid currently is itaconic acid due to its commercial availability or citramalic acid.

A suitable pre-cursor is one which can be re-cycled to produce one or more of the said dicarboxylic acids. Typically, the pre-cursor will decompose under suitable conditions of temperature and pressure to produce the said dicarboxylic acids. Accordingly, the pre-cursor may be regarded as a source of the dicarboxylic acid. It will be appreciated that a base catalyst is already present so that the pre-cursor decomposition may advantageously be base catalysed under such suitable conditions. A suitable pre-cursor for the itaconic, citraconic, mesaconic or citramalic acids is citric acid which may be dehydrated and decarboxylated to produce at least one of itaconic, citraconic, mesaconic acids or decarboxylated to produce citramalic acid. This reaction takes place under suitable conditions of temperature and pressure and optionally in the presence of the base catalyst without the necessity of a further separate catalyst. However, it has been found that adding citric acid to the aqueous medium/reaction medium prior to extraction also assists the extraction of the methacrylic acid as the added acid whilst also not introducing an external reagent which itself needs to be removed from the aqueous medium/reaction medium because the citric acid can then be treated subsequently to generate more dicarboxylic acid and thence methacrylic acid in a continuous process.

According to a third aspect of the present invention there is provided a process for the production of (meth)acrylic acid comprising the steps of:— forming an aqueous medium of at least one base catalyst and at least one dicarboxylic acid selected from fumaric, maleic, malic, itaconic, citraconic, mesaconic or citramalic acid or mixtures thereof;

decarboxylating the at least one dicarboxylic acid in the presence of the at least one base catalyst under suitable conditions of temperature and pressure to produce (meth)acrylic acid and/or base salts thereof in the aqueous medium;

introducing an organic solvent to the said aqueous medium for solvent extraction of the (meth)acrylic acid into an organic phase;

characterised in that the level of base catalyst to the said at least one dicarboxylic acid and/or pre-cursor thereof is maintained at a sub-stoichiometric level in relation to the formation of the first acid salt thereof during the extraction process.

In any aspect herein, the organic solvent may be introduced to the aqueous medium before or after decarboxylation.

Preferably, the sub-stoichiometric level is maintained, after, if necessary, being implemented post reaction by added acid, during at least that part of the extraction process herein which is carried out after the decarboxylation step.

According to a fourth aspect of the present invention there is provided a process for the production of (meth)acrylic acid comprising the steps of:— forming an aqueous medium of at least one base catalyst and at least one dicarboxylic acid selected from fumaric, maleic, malic, itaconic, citraconic, mesaconic or citramalic acid or mixtures thereof;

decarboxylating the at least one dicarboxylic acid in the presence of the at least one base catalyst under suitable conditions of temperature and pressure to produce (meth)acrylic acid and/or base salts thereof in the aqueous medium;

introducing an organic solvent to the said aqueous medium for solvent extraction of the (meth)acrylic acid into an organic phase;

characterised by the step of adding an additional amount of at least one of the said dicarboxylic acids and/or a pre-cursor thereof to the said aqueous medium, preferably, after the decarboxylation step to enhance the solvent extraction of the (meth)acrylic acid into the organic phase.

Advantageously, in accordance with some embodiments of the invention, it is also possible to maintain the level of base catalyst to the said at least one dicarboxylic acid and/or pre-cursor thereof at a sub-stoichiometric level in relation to the formation of the first acid salt thereof during the decarboxylation.

Suitable organic solvents for (meth)acrylic acid extraction include hydrocarbon solvents or oxygenated solvents, particularly $C_4$-$C_{20}$ hydrocarbon solvents. The hydrocarbon solvents may be aliphatic, aromatic, or part aromatic, saturated or unsaturated, cyclic, acyclic or part cyclic, linear or branched. The oxygenated solvents may be esters, ethers or ketones. Suitable solvents include toluene, benzene, ethylbenzene, xylene, trimethylbenzene, octane, heptane, hexane, pentane, cyclopentane, cyclohexane, cycloheptane, cyclooctane, cyclohexene, methylcyclohexane, methylethylketone, methyl methacrylate or mixtures thereof. Ionic liquids which are immiscible with water may also be used.

A preferred mixture of solvents for the extraction of MAA is a $C_4$-$C_{20}$ hydrocarbon solvent and MMA. A suitable mixture contains 1-40% MMA, more typically, 5-30% MMA with the balance made up of the hydrocarbon solvent(s). Preferred hydrocarbon solvents for this purpose are toluene and xylenes.

Nevertheless, it is preferred to use only $C_4$-$C_{20}$ hydrocarbons either alone or in mixtures with other hydrocarbons as the extractive solvent. Preferably, the relative (static) permittivity of the hydrocarbon or each of the hydrocarbons in a mixture of hydrocarbons is less than 20, more preferably, less than 8, most preferably, less than 3 at 20° C. and atmospheric pressure. Accordingly, hydrocarbons having relative (static) permittivity in the range 1.6 to 20 are preferred, more preferably in the range 1.7 to 8, most preferably, in the range 1.8 to 3 at 20° C. and atmospheric pressure.

The preferred solvents and mixtures for extraction of AA have relative (static) permittivity of less than 20, more preferably, less than 10, most preferably, less than 7 at 20° C. and atmospheric pressure. Typically, the relative (static) permittivity is at least 1.6, more typically, at least, 2.0, most typically, at least, 2.3. Accordingly, solvents having relative (static) permittivity in the range 1.6 to 20 are preferred, more preferably in the range 2.0 to 10, most preferably, in the range 2.2 to 8 all at 20° C. and atmospheric pressure.

The dicarboxylic acid(s) reactants and the base catalyst need not necessarily be the only compounds present in the aqueous medium/reaction medium. The dicarboxylic acid(s) together with any other compounds present are generally dissolved in an aqueous solution for the base catalysed thermal decarboxylation.

Preferably, the base catalysed decarboxylation of the at least one dicarboxylic acid takes place at less than 350° C., typically, less than 330° C., more preferably, at up to 310° C., most preferably at up to 300° C. In any case, a preferred lower temperature for the decarboxylation process of the present invention is 200° C. Preferred temperature ranges for the decarboxylation process of the present invention are between 200 and up to 349° C., more preferably, between 220 and 320° C., most preferably, between 240 and 310° C., especially between 240 and 290° C. An especially preferred temperature range is 240-275° C., most especially, 245-275° C.

The base catalysed decarboxylation reaction takes place at a temperature at which the aqueous medium/reaction medium is in the liquid phase. Typically, the aqueous medium/reaction medium is an aqueous solution.

Preferably, the base catalysed decarboxylation takes place with the dicarboxylic acid reactants and preferably the base catalyst in aqueous solution.

Advantageously, carrying out the decarboxylation at lower temperatures prevents the production of significant amounts of by-products which may be difficult to remove and may cause further purification and processing problems in an industrial process. Therefore, the process provides a surprisingly improved selectivity in this temperature range. Furthermore, lower temperature decarboxylation uses less energy and thereby creates a smaller carbon footprint than high temperature decarboxylations.

Preferably, the extraction step of the (meth)acrylic acid takes place at less than or equal to the decarboxylation temperatures detailed above, more preferably however at less than 100° C., most preferably, at less than 80° C., especially less than 60° C. In any case, a preferred lower temperature for the extraction step of the present invention is −10° C., more preferably, 0° C. Preferred temperature ranges for the extraction step of the present invention are between −10 and up to 349° C., more preferably, between −10 and 100° C., most preferably, between 0 and 80° C., especially between 10 and 60° C., more especially 30-50° C.

The extraction step takes place at a temperature at which the organic and aqueous phases are in the liquid phase.

Accordingly, the extraction step takes place at a pressure at which the organic and aqueous phases are in the liquid phase, generally, extraction takes place at atmospheric pressure.

The dicarboxylic acids are available from non-fossil fuel sources. For instance, the itaconic, citramalic, citraconic or mesaconic acids could be produced from pre-cursors such as citric acid or isocitric acid by dehydration and decarboxylation at suitably high temperatures or from aconitic acid by decarboxylation at suitably high temperatures. It will be appreciated that a base catalyst is already present so that the pre-cursor may be subjected to base catalysed dehydration and/or decomposition. Citric acid and isocitric acid may themselves be produced from known fermentation processes and aconitic acid may be produced from the former acids. Accordingly, the process of the invention goes some way to providing a biological or substantially biological route to generate (meth)acrylates directly whilst minimising reliance on fossil fuels.

U.S. Pat. No. 5,849,301 discloses a process for production of malic and fumaric acids from glucose. U.S. Pat. No. 5,766,439 discloses a process for production of maleic acid. Malic acid is also available by extraction of products produced in agriculture such as apple juice.

To maintain the reactants in the liquid phase under the above temperature conditions the decarboxylation reaction of the at least one dicarboxylic acid is carried out at suitable pressures in excess of atmospheric pressure. Suitable pressures which will maintain the reactants in the liquid phase in the above temperature ranges are greater than 200 psi, more suitably, greater than 300 psi, most suitably, greater than 450 psi and in any case at a higher pressure than that below which the reactant medium will boil. There is no upper limit of pressure but the skilled person will operate within practical limits and within apparatus tolerances, for instance, at less than 10,000 psi, more typically, at less than 5,000 psi, most typically, at less than 4000 psi.

Preferably, the above decarboxylation reaction is at a pressure of between about 200 and 10000 psi. More preferably, the reaction is at a pressure of between about 300 and 5000 psi and yet more preferably between about 450 and 3000 psi.

In a preferred embodiment, the above reaction is at a pressure at which the aqueous medium/reaction medium is in the liquid phase.

The above reaction is at a temperature and pressure at which the aqueous medium/reaction medium is in the liquid phase.

As mentioned above, the catalyst is a base catalyst.

Preferably, the catalyst comprises a source of $OH^-$ ions.

Preferably, the base catalyst comprises a metal oxide, hydroxide, carbonate, acetate (ethanoate), alkoxide, hydrogencarbonate or salt of a decomposable di- or tri-carboxylic acid, or a quaternary ammonium compound of one of the above; more preferably a Group I or Group II metal oxide, hydroxide, carbonate, acetate, alkoxide, hydrogencarbonate or salt of a di- or tri-carboxylic acid or (meth)acrylic acid. The base catalyst may also comprise one or more amines.

Preferably, the base catalyst is selected from one or more of the following: LiOH, NaOH, KOH, $M(OH)_2$, $Ca(OH)_2$, $Ba(OH)_2$, CsOH, $Sr(OH)_2$, RbOH, $NH_4OH$, $Li_2CO_3$, $Na_2CO_3$, $K_2CO_3$, $Rb_2CO_3$, $Cs_2CO_3$, $MgCO_3$, $CaCO_3$, $SrCO_3$, $BaCO_3$, $(NH_4)_2CO_3$, $LiHCO_3$, $NaHCO_3$, $KHCO_3$, $RbHCO_3$, $CsHCO_3$, $Mg(HCO_3)_2$, $Ca(HCO_3)_2$, $Sr(HCO_3)_2$, $Ba(HCO_3)_2$, $NH_4HCO_3$, $Li_2O$, $Na_2O$, $K_2O$, $Rb_2O$, $Cs_2O$, MgO, CaO, SrO, BaO, $Li(OR^1)$, $Na(OR^1)$, $K(OR^1)$, $Rb(OR^1)$, $Cs(OR^1)$, $Mg(OR^1)_2$, $Ca(OR^1)_2$, $Sr(OR^1)_2$, Ba(OR$^1$)$_2$, NH$_4$(OR$^1$) where R$^1$ is any C$_1$ to C$_6$ branched, unbranched or cyclic alkyl group, being optionally substituted with one or more functional groups; NH$_4$(RCO$_2$), Li(RCO$_2$), Na(RCO$_2$), K(RCO$_2$), Rb(RCO$_2$), Cs(RCO$_2$), Mg(RCO$_2$)$_2$, Ca(RCO$_2$)$_2$, Sr(RCO$_2$)$_2$ or Ba(RCO$_2$)$_2$, where RCO$_2$ is selected from malate, fumarate, maleate, citramalate, mesaconate, citraconate, itaconate, citrate, oxalate and (meth)acrylate; (NH$_4$)$_2$(CO$_2$RCO$_2$), Li$_2$(CO$_2$RCO$_2$), Na$_2$(CO$_2$RCO$_2$), K$_2$(CO$_2$RCO$_2$), Rb$_2$(CO$_2$RCO$_2$), Cs$_2$(CO$_2$RCO$_2$), Mg(CO$_2$RCO$_2$), Ca(CO$_2$RCO$_2$), Sr(CO$_2$RCO$_2$), Ba(CO$_2$RCO$_2$), (NH$_4$)$_2$(CO$_2$RCO$_2$), where CO$_2$RCO$_2$ is selected from malate, fumarate, maleate, citramalate, mesaconate, citraconate, itaconate and oxalate; (NH$_4$)$_3$(CO$_2$R(CO2)CO$_2$), Li$_3$(CO$_2$R(CO$_2$)CO$_2$), Na$_3$(CO$_2$R(CO2)CO$_2$), K$_3$(CO$_2$R(CO$_2$)CO$_2$), Rb$_3$(CO$_2$R(CO$_2$)CO$_2$), Cs$_3$(CO$_2$R(CO$_2$)CO$_2$), Mg$_3$(CO$_2$R(CO$_2$)CO$_2$)$_2$, Ca$_3$(CO$_2$R(CO$_2$)CO$_2$)$_2$, Sr$_3$(CO$_2$R(CO$_2$)CO$_2$)$_2$, Ba$_3$(CO$_2$R(CO$_2$)CO$_2$)$_2$, (NH$_4$)$_3$(CO$_2$R(CO$_2$)CO$_2$), where CO$_2$R(CO$_2$)CO$_2$ is selected from citrate, isocitrate and aconitate; methylamine, ethylamine, propylamine, butylamine, pentylamine, hexylamine, cyclohexylamine, aniline; and R$_4$NOH where R is selected from methyl, ethyl propyl, butyl. More preferably, the base is selected from one or more of the following: LiOH, NaOH, KOH, Mg(OH)$_2$, Ca(OH)$_2$, Ba(OH)$_2$, CsOH, Sr (OH)$_2$, RbOH, NH$_4$OH, Li$_2$CO$_3$, Na$_2$CO$_3$, K$_2$CO$_3$, Rb$_2$CO$_3$, Cs$_2$CO$_3$, MgCO$_3$, CaCO$_3$, (NH$_4$)$_2$CO$_3$, LiHCO$_3$, NaHCO$_3$, KHCO$_3$, RbHCO$_3$, CsHCO$_3$, Mg(HCO$_3$)$_2$, Ca(HCO$_3$)$_2$, Sr(HCO$_3$)$_2$, Ba(HCO$_3$)$_2$, NH$_4$HCO$_3$, Li$_2$O, Na$_2$O, K$_2$O, Rb$_2$O, Cs$_2$O,; NH$_4$(RCO$_2$), Li(RCO$_2$), Na(RCO$_2$), K(RCO$_2$), Rb(RCO$_2$), Cs(RCO$_2$), Mg(RCO$_2$)$_2$, Ca(RCO$_2$)$_2$, Sr(RCO$_2$)$_2$ or Ba(RCO$_2$)$_2$, where RCO$_2$ is selected from malate, fumarate, maleate, itaconate, citrate, oxalate, (meth)acrylate; (NH$_4$)$_2$(CO$_2$RCO$_2$), Li$_2$(CO$_2$RCO$_2$), Na$_2$(CO$_2$RCO$_2$), K$_2$(CO$_2$RCO$_2$), Rb$_2$(CO$_2$RCO$_2$), Cs$_2$(CO$_2$RCO$_2$), Mg(CO$_2$RCO$_2$), Ca(CO$_2$RCO$_2$), Sr(CO$_2$RCO$_2$), Ba(CO$_2$RCO$_2$), (NH$_4$)$_2$(CO$_2$RCO$_2$), where CO$_2$RCO$_2$ is selected from malate, fumarate, maleate, citramalate, mesaconate, citraconate, itaconate, oxalate; (NH$_4$)$_3$(CO$_2$R(CO2)CO$_2$), Li$_3$(CO$_2$R(CO$_2$)CO$_2$), Na$_3$(CO$_2$R(CO2)CO$_2$), K$_3$(CO$_2$R(CO$_2$)CO$_2$), Rb$_3$(CO$_2$R(CO$_2$)CO$_2$), Cs$_3$(CO$_2$R(CO$_2$)CO$_2$), Mg$_3$(CO$_2$R(CO$_2$)CO$_2$)$_2$, Ca$_3$(CO$_2$R(CO$_2$)CO$_2$)$_2$, Sr$_1$(CO$_2$R(CO$_2$)CO$_2$)$_2$, Ba$_3$(CO$_2$R(CO$_2$)CO$_2$)$_2$, (NH$_4$)$_3$(CO$_2$R(CO$_2$)CO$_2$), where CO$_2$R(CO$_2$)CO$_2$ is selected from citrate, isocitrate; tetramethylammonium hydroxide and tetraethylammonium hydroxide. Most preferably, the base is selected from one or more of the following: NaOH, KOH, Ca(OH)$_2$, CsOH, RbOH, NH$_4$OH, Na$_2$CO$_3$, K$_2$CO$_3$, Rb$_2$CO$_3$, Cs$_2$CO$_3$, MgCO$_3$, CaCO$_3$, (NH$_4$)$_2$CO$_3$, NH$_4$(RCO$_2$), Na(RCO$_2$), K(RCO$_2$), Rb(RCO$_2$), Cs(RCO$_2$), Mg(RCO$_2$)$_2$, Ca(RCO$_2$)$_2$, Sr(RCO$_2$)$_2$ or Ba(RCO$_2$)$_2$, where RCO$_2$ is selected from malate, fumarate, maleate, itaconate, citrate, oxalate, (meth)acrylate; (NH$_4$)$_2$(CO$_2$RCO$_2$), Na$_2$(CO$_2$RCO$_2$), K$_2$(CO$_2$RCO$_2$), Rb$_2$(CO$_2$RCO$_2$), Cs$_2$(CO$_2$RCO$_2$), Mg(CO$_2$RCO$_2$), Ca(CO$_2$RCO$_2$), (NH$_4$)$_2$(CO$_2$RCO$_2$), where CO$_2$RCO$_2$ is selected from malate, fumarate, maleate, citramalate, mesaconate, citraconate, itaconate, oxalate; (NH$_4$)$_3$(CO$_2$R(CO2)CO$_2$), Na$_3$(CO$_2$R(CO2)CO$_2$), K$_3$(CO$_2$R(CO$_2$)CO$_2$), Rb$_3$(CO$_2$R(CO$_2$)CO$_2$), Cs$_3$(CO$_2$R(CO$_2$)CO$_2$), Mg$_3$(CO$_2$R(CO$_2$)CO$_2$)$_2$, Ca$_3$(CO$_2$R(CO$_2$)CO$_2$)$_2$, (NH$_4$)$_3$(CO$_2$R(CO$_2$)CO$_2$), where CO$_2$R(CO$_2$)CO$_2$ is selected from citrate, isocitrate; and tetramethylammonium hydroxide.

The catalyst may be homogeneous or heterogeneous. In one embodiment, the catalyst may be dissolved in a liquid reaction phase. However, the catalyst may be suspended on a solid support over which the reaction phase may pass. In this scenario, the reaction phase is preferably maintained in a liquid, more preferably, an aqueous phase.

Preferably, the effective mole ratio of base OH$^-$:acid for the decarboxylation reaction is between 0.001-2:1, more preferably, 0.01-1.2:1, most preferably, 0.1-1:1, especially, 0.3-1:1. By the effective mole ratio of base OH$^-$ is meant the nominal molar content of OH derived from the compounds concerned.

By acid is meant the moles of acid. Thus, in the case of a monobasic base, the effective mole ratios of base OH$^-$:acid will coincide with those of the compounds concerned but in the case of di or tribasic bases the effective mole ratio will not coincide with that of mole ratio of the compounds concerned.

Specifically, this may be regarded as the mole ratio of monobasic base: di or tri carboxylic acid is preferably between 0.001-2:1, more preferably, 0.01-1.2:1, most preferably, 0.1-1:1, especially, 0.3-1:1.

As the deprotonation of the acid to form the salt is only referring to a first acid deprotonation in the present invention, in the case of di or tribasic bases, the mole ratio of base above will vary accordingly.

Optionally, the (meth)acrylic acid product may be esterified to produce an ester thereof. Potential esters may be selected from C$_1$-C$_{12}$ alkyl or C$_2$-C$_{12}$ hydroxyalkyl, glycidyl, isobornyl, dimethylaminoethyl, tripropyleneglycol esters. Most preferably the alcohols or alkenes used for forming the esters may be derived from bio sources, e.g. biomethanol, bioethanol, biobutanol.

As mentioned above, the pre-cursor such as citric acid, isocitric acid or aconitic acid preferably decomposes under suitable conditions of temperature and pressure and optionally in the presence of base catalyst to one of the dicarboxylic acids of the invention. Suitable conditions for this decomposition are less than 350° C., typically, less than 330° C., more preferably, at up to 310° C., most preferably at up to 300° C. In any case, a preferred lower temperature for the decomposition is 180° C. Preferred temperature ranges for the pre-cursor decomposition are between 190 and up to 349° C., more preferably, between 200 and 300° C., most preferably, between 220 and 280° C., especially between 220 and 260° C.

The pre-cursor decomposition reaction takes place at a temperature at which the aqueous reaction medium is in the liquid phase.

To maintain the reactants in the liquid phase under the above pre-cursor decomposition temperature conditions the decarboxylation reaction is carried out at suitable pressures in excess of atmospheric pressure. Suitable pressures which will maintain the reactants in the liquid phase in the above temperature ranges are greater than 150 psi, more suitably, greater than 180 psi, most suitably, greater than 230 psi and in any case at a higher pressure than that below which the reactant medium will boil. There is no upper limit of pressure but the skilled person will operate within practical limits and within apparatus tolerances, for instance, at less than 10,000 psi, more typically, at less than 5,000 psi, most typically, at less than 4000 psi.

Preferably, the pre-cursor decomposition reaction is at a pressure of between about 150 and 10000 psi. More preferably, the reaction is at a pressure of between about 180 and 5000 psi and yet more preferably between about 230 and 3000 psi.

In a preferred embodiment, the pre-cursor decomposition reaction is at a pressure at which the reaction medium is in the liquid phase.

Preferably, the pre-cursor decomposition reaction is at a temperature and pressure at which the aqueous reaction medium is in the liquid phase.

According to a further aspect of the present invention there is provided a method of preparing polymers or copolymers of (meth)acrylic acid or (meth)acrylic acid esters, comprising the steps of
(i) preparation of (meth)acrylic acid in accordance with the third or fourth aspect of the present invention;
(ii) optional esterification of the (meth)acrylic acid prepared in (i) to produce the (meth)acrylic acid ester;
(iii) polymerisation of the (meth)acrylic acid prepared in (i) and/or the ester prepared in (ii), optionally with one or more comonomers, to produce polymers or copolymers thereof.

Preferably, the (meth)acrylic acid ester of (ii) above is selected from $C_1$-$C_{12}$ alkyl or $C_2$-$C_{12}$ hydroxyalkyl, glycidyl, isobornyl, dimethylaminoethyl, tripropyleneglycol esters, more preferably, ethyl, n-butyl, i-butyl, hydroxymethyl, hydroxypropyl or methyl methacrylate, most preferably, methyl methacrylate, ethyl acrylate, butyl methacrylate or butyl acrylate.

Advantageously, such polymers will have an appreciable portion if not all of the monomer residues derived from a source other than fossil fuels.

In any case, preferred comonomers include for example, monoethylenically unsaturated carboxylic acids and dicarboxylic acids and their derivatives, such as esters, amides and anhydrides.

Particularly preferred comonomers are acrylic acid, methyl acrylate, ethyl acrylate, propyl acrylate, n-butyl acrylate, iso-butyl acrylate, t-butyl acrylate, 2-ethylhexyl acrylate, hydroxyethyl acrylate, iso-bornyl acrylate, methacrylic acid, methyl methacrylate, ethyl methacrylate, propyl methacrylate, n-butyl methacrylate, iso-butyl methacrylate, t-butyl methacrylate, 2-ethylhexyl methacrylate, hydroxyethyl methacrylate, lauryl methacrylate, glycidyl methacrylate, hydroxypropyl methacrylate, iso-bornyl methacrylate, dimethylaminoethyl methacrylate, tripropyleneglycol diacrylate, styrene, α-methyl styrene, vinyl acetate, isocyanates including toluene diisocyanate and p,p'-methylene diphenyl diisocyanate, acrylonitrile, butadiene, butadiene and styrene (MBS) and ABS subject to any of the above comonomers not being the monomer selected from methacrylic acid or a methacrylic acid ester in (i) or (ii) above in any given copolymerisation of the said acid monomer in (i) or a said ester monomer in (ii) with one or more of the comonomers.

It is of course also possible to use mixtures of different comonomers. The comonomers themselves may or may not be prepared by the same process as the monomers from (i) or (ii) above.

According to a further aspect of the present invention there is provided polyacrylic acid, polymethacrylic acid, polyalkylacrylate, polymethylmethacrylate (PMMA) and polybutylmethacrylate homopolymers or copolymers formed from the method of preparing polymers or copolymers of the above aspect.

According to a still further aspect of the present invention there is provided a process for the production of methacrylic acid comprising:—
providing a source of a pre-cursor acid selected from aconitic, citric and/or isocitric acid;
performing a decarboxylation and, if necessary, a dehydration step on the source of pre-cursor acid by exposing the source thereof in the presence or absence of base catalyst to a sufficiently high temperature to provide itaconic, mesaconic, citraconic and/or citramalic acid; and
use of the itaconic, mesaconic, citraconic and/or citramalic acid provided in a process according to any of the other aspects of the present invention to provide methacrylic acid and/or enhance extraction thereof into an organic phase.

By a source of aconitic, citric and/or isocitric acid is meant the acids and salts thereof such as group I or II metal salts thereof and includes solutions of the pre-cursor acids and salts thereof, such as aqueous solutions thereof.

Optionally, the salt may be acidified to liberate the free acid prior to, during or after the pre-cursor acid decarboxylation step.

Preferably, the dicarboxylic acid(s) reactant(s) or the pre-cursors thereof of the present invention are exposed to the reaction conditions for a suitable time period to effect the required reaction, typically, for a time period of at least 30 seconds, more preferably at least about 100 seconds, yet more preferably at least about 120 seconds and most preferably at least about 150 seconds.

Typically, the dicarboxylic acid(s) reactant(s) or pre-cursors thereof are exposed to the reaction conditions for a time period of less than about 2000 seconds, more typically less than about 1500 seconds, yet more typically less than about 1000 seconds.

Preferably, the dicarboxylic acid(s) reactant(s) or the pre-cursors thereof of the present invention are exposed to the reaction conditions for a time period of between about 75 seconds and 2500 seconds, more preferably between about 90 seconds and 1800 seconds and most preferably between about 120 seconds and 800 seconds.

Preferably, the dicarboxylic acid(s) reactant(s) or the pre-cursors thereof of the present invention are dissolved in water so that the reaction occurs under aqueous conditions.

It will be clear from the way in which the above reactions are defined that if the pre-cursor is decarboxylated and, if necessary, dehydrated in a reaction medium then the reaction medium may simultaneously be effecting base catalysed decarboxylation of the at least one dicarboxylic acid selected from maleic, fumaric, malic, itaconic, citraconic, mesaconic, citramalic acid or mixtures thereof produced from the pre-cursor thereof according to any aspect of the invention. Accordingly, the decarboxylation and if necessary, dehydration of the pre-cursor and the base catalysed decarboxylation of the at least one dicarboxylic acid may take place in one reaction medium i.e. the two processes may take place as a one pot process. However, it is preferred if the pre-cursor is decarboxylated and, if necessary, dehydrated substantially without base catalysis so that the decarboxylation and if necessary, dehydration of the pre-cursor and the base catalysed decarboxylation of the at least one dicarboxylic acid take place in separate steps.

Preferably, the concentration of the dicarboxylic acid reactant(s) in the decarboxylation reaction is at least 0.1M, preferably in an aqueous source thereof; more preferably at least about 0.2M, preferably in an aqueous source thereof; most preferably at least about 0.3M, preferably in an aqueous source thereof, especially, at least about 0.5M. Generally, the aqueous source is an aqueous solution.

Preferably, the concentration of the dicarboxylic acid reactant(s) in the decarboxylation reaction is less than about 10M, more preferably, less than 8M, preferably in an aqueous source thereof; more preferably, less than about 5M, preferably in an aqueous source thereof; more preferably less than about 3M, preferably in an aqueous source thereof.

Preferably, the concentration of the dicarboxylic acid reactant(s) in the decarboxylation reaction is in the range 0.05M-20, typically, 0.05-10M, more preferably, 0.1M-5M, most preferably, 0.3M-3M.

The base catalyst may be dissolvable in a liquid medium, which may be water or the base catalyst may be heterogeneous. The base catalyst may be dissolvable in the aqueous medium/reaction medium so that reaction is effected by exposing the reactants to a temperature in excess of that at which base catalysed decarboxylation of the reactant(s) to (meth)acrylic acid and/or the pre-cursor acids to the dicarboxylic acids will occur such as those temperatures given above. The catalyst may be in an aqueous solution. Accordingly, the catalyst may be homogenous or heterogeneous but is typically homogenous. Preferably, the concentration of the catalyst in the aqueous medium/reaction medium (including the decomposition of pre-cursor acid medium) is at least 0.1M or greater, preferably in an aqueous source thereof; more preferably at least about 0.2M, preferably in an aqueous source thereof; more preferably at least about 0.3M.

Preferably, the concentration of the catalyst in the aqueous medium/reaction medium (including the decomposition of pre-cursor acid medium) is less than about 10M, more preferably, less than about 5M, more preferably less than about 2M and, in any case, preferably less than or equal to that which would amount to a saturated solution at the temperature and pressure of the reaction.

Preferably, the mole concentration of OH⁻ in the aqueous medium/reaction medium or pre-cursor acid decomposition is in the range 0.05M-20M, more preferably, 0.1-5M, most preferably, 0.2M-2M.

Preferably, the reaction conditions are weakly acidic. Preferably, the reaction pH is between about 2 and 9, more preferably between about 3 and about 6.

For the avoidance of doubt, by the term itaconic acid, is meant the following compound of formula (i)

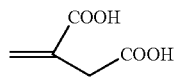

(i)

For the avoidance of doubt, by the term citraconic acid, is meant the following compound of formula (ii)

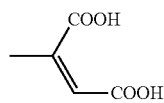

(ii)

For the avoidance of doubt, by the term mesaconic acid, is meant the following compound of formula (iii)

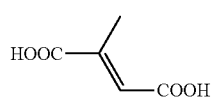

(iii)

For the avoidance of doubt, by the term citramalic acid, is meant the following compound of formula (iv)

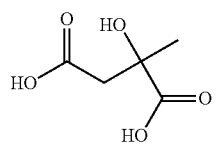

(iv)

As mentioned above, the processes of the present invention may be homogenous or heterogeneous. In addition, the process may be a batch or continuous process.

Advantageously, one by-product in the production of MAA may be hydroxy isobutyric acid (HIB) which exists in equilibrium with the product MAA at the conditions used for decomposition of the dicarboxylic acids. Accordingly, partial or total separation of the MAA from the products of the decomposition reaction shifts the equilibrium from HIB to MAA thus generating further MAA during the extraction process or in subsequent processing of the solution after separation of MAA. Optionally the solvent may be present during the decomposition reaction so that a portion at least of the methacrylic acid is extracted into the organic medium during the decomposition reaction.

Advantageously, one by-product in the production of AA may be hydroxy propionic acid (HPA) which exists in equilibrium with the product AA at the conditions used for decomposition of the dicarboxylic acids. Accordingly, partial or total separation of the AA from the products of the decomposition reaction shifts the equilibrium from HPA to AA thus generating further AA during the extraction process or in subsequent processing of the solution after separation of AA. Optionally the solvent may be present during the decomposition reaction so that a portion at least of the acrylic acid is extracted into the organic medium during the decomposition reaction.

Where a compound of a formula herein may exist as more than one stereoisomer, for example a compound of formula (Iv) above, all stereoisomers are included within the scope of the invention. In particular, R+ or S– forms of citramalic acid as well as racemic mixtures thereof are included within the scope of the term citramalic acid.

All of the features contained herein may be combined with any of the above aspects, in any combination.

A BRIEF DESCRIPTION OF THE DRAWINGS

For a better understanding of the invention, and to show how embodiments of the same may be carried into effect, reference will now be made, by way of example, to the following figures and examples in which:—

SOLVENT EXTRACTION

The following experimental conditions were used unless indicated otherwise:—
0.1M Acids
1:1 vol:vol aq:solvent
Room Temperature
1 minutes agitation time; 5 min settling time
Solvent is toluene unless where stated
Analysis by HPLC

COMPARATIVE EXAMPLE 1

A series of solvents were tested to examine the extent of transfer of methacrylic acid from an aqueous solution using the above procedure. The results are shown in table 1.

TABLE 1

| Solvent | Average % Transfer | relative (static) permittivity |
|---|---|---|
| Mixed Xylenes | 45.3 | 2.3 |
| Toluene | 48.2 | 2.4 |
| Hexane | 27.6 | 1.9 |
| Benzene | 50.1 | 2.3 |
| Pentane | 28.3 | 1.8 |
| Cyclohexane | 26.9 | 2.0 |
| MMA | 84.3 | 6.3 |

This example shows that MAA present in the free acid form can be efficiently extracted into a range of solvents. Aromatic hydrocarbons give the highest extraction efficiencies.

COMPARATIVE EXAMPLE 2

Monobasic and dibasic acids likely to be present in aqueous solution following partial decomposition of mono and dicarboxylic acids expected to be found from decomposition of dibasic or tribasic acids were compared for their solubility in toluene.

Each acid, initially at 0.1M solution in water was separately tested for solubility in an equal volume of toluene. The results are shown in table 2

TABLE 2

| Acid | Fraction Transferred to Toluene/% |
|---|---|
| monobasic | |
| MAA | 54.4 |
| CT | 40.11 |
| HIB | 4.21 |
| PY | 0 |
| dibasic | |
| IC | 0 |
| MC | 0.64 |

MAA Methacrylic Acid
CT Crotonic Acid
HIB Hydroxyisobutyric Acid
PY Pyruvic Acid
IC Itaconic Acid
MC Mesaconic Acid This example shows that the di and tricarboxylic acids useful in the process for the production of MAA are not soluble in toluene, one solvent which can be employed for the extraction of MAA. Furthermore HIB formed in equilibrium with MAA is not extracted in significant proportions and pyruvic acid formed as an unwanted by-product is also not extracted into toluene.

COMPARATIVE EXAMPLE 3

A series of different concentrations of MAA in aqueous solution were extracted into toluene (1:1 by volume vs aqueous solution). The percentage solubility is shown in table 3.

TABLE 3

| | [MAA] in starting aq soln/M | % extracted at 1:1 toluene to aq soln |
|---|---|---|
| Comp Ex 3a | 0.00743 | 12.69% |
| Comp Ex 3b | 0.0148 | 20.07% |
| Comp Ex 3c | 0.02878 | 26.76% |
| Comp Ex 3d | 0.05829 | 37.09% |
| Comp Ex 3e | 0.1215 | 52.00% |
| Comp Ex 3f | 0.2479 | 60.51% |
| Comp Ex 3g | 0.3 | 63.60% |
| Comp Ex 3h | 0.4778 | 68.67% |
| Comp Ex 3j | 0.7559 | 73.72% |
| Comp Ex 3k | 0.9576 | 76.71% |

Figure 1:
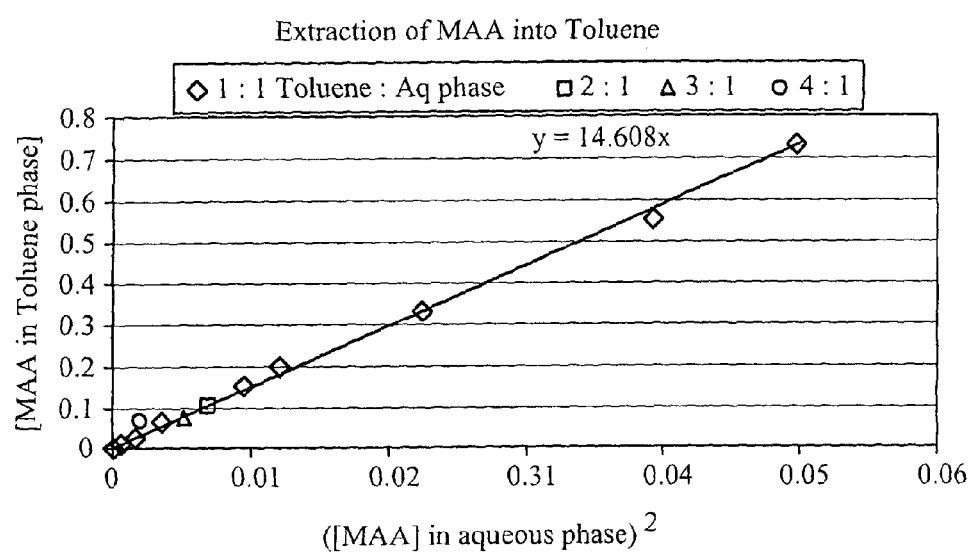
FIG. 1 shows the concentration dependence of the extraction of MAA into toluene.

The fraction transferred increases with the concentration of MAA. The data from table 3 were plotted according to the equation:

$$[MAA]_{tol} = K[MAA]^2_{aq}$$

and the value K in the equation was evaluated as 14.6. The results are plotted in FIG. 1.

This example shows that the extraction of MAA into toluene is concentration dependent. For efficient extraction, concentrations above 0.1M are preferred.

COMPARATIVE EXAMPLE 4

Aqueous solutions were prepared of each of the dicarboxylic acids exemplified in comparative example 2.

These were extracted with an equal volume of solvent mixtures of toluene and methyl methacrylate (MMA). The resultant degrees of extraction are shown in table 4

TABLE 4

| Fraction of MMA in MMA/Toluene solvent mixture | IC | MC | PY | MAA | HIB | CT |
|---|---|---|---|---|---|---|
| 0 | 0 | 0.64 | 0 | 54.4 | 4.21 | 40.11 |
| 0.1 | 0 | 1.72 | 0 | 58.85 | 4.8 | 46.72 |
| 0.2 | 0.29 | 4.5 | 0.3 | 63.01 | 5.14 | 49.88 |
| 0.3 | 0.81 | 8.26 | 0.7 | 67.25 | 6.38 | 53.62 |
| 0.4 | 1.69 | 13.02 | 1.17 | 70.31 | 4.82 | 56.56 |
| 0.5 | 2.89 | 20.56 | 2.07 | 74.28 | 5.76 | 61.15 |
| 0.6 | 4.34 | 27.82 | 3.01 | 76.77 | 7.32 | 64.67 |
| 0.7 | 6.56 | 38.06 | 4.17 | 79.42 | 19.71 | 68.07 |
| 0.8 | 9.57 | 47.19 | 5.57 | 81.42 | 21.47 | 70.86 |
| 0.9 | 13.1 | 56.33 | 8.05 | 83.02 | 23.32 | 73.21 |
| 1 | 17.58 | 63.45 | 10.71 | 84.28 | 23.9 | 75.05 |

This example shows that MMA can be added to toluene to improve the extraction efficiency of MAA. However an optimum MMA level is observed above which dicarboxylic acids and HIB are extracted in significant amounts.

In order to compare the solubilities in the organic solvents in terms of partition coefficients each sample was converted to a partition coefficient based on the equation:

$$[MAA]_{solv} = K[MAA]^2_{aq}$$

Figure 2:
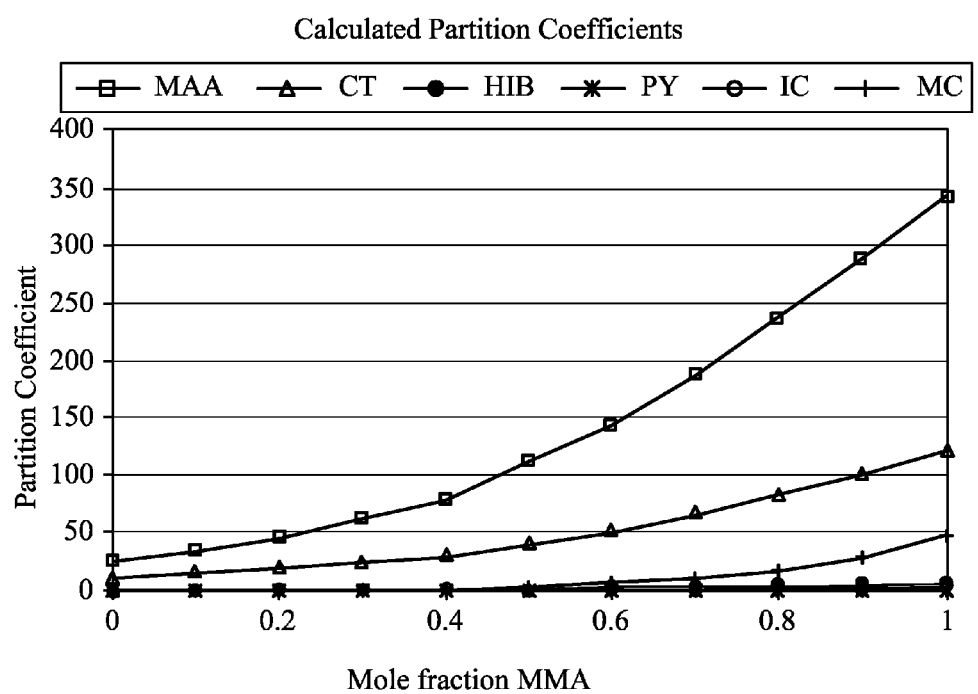
FIG. 2 shows a plot of partition coefficient for a range of acids against MMA fraction in toluene.

The data are presented in FIG. 2

Only MAA, Crotonic acid and hydroxyisobutyric acid have significant solubilities in any of the solvent phases.

The solubility of the components increases with the fraction of MMA in every case.

Figure 3:
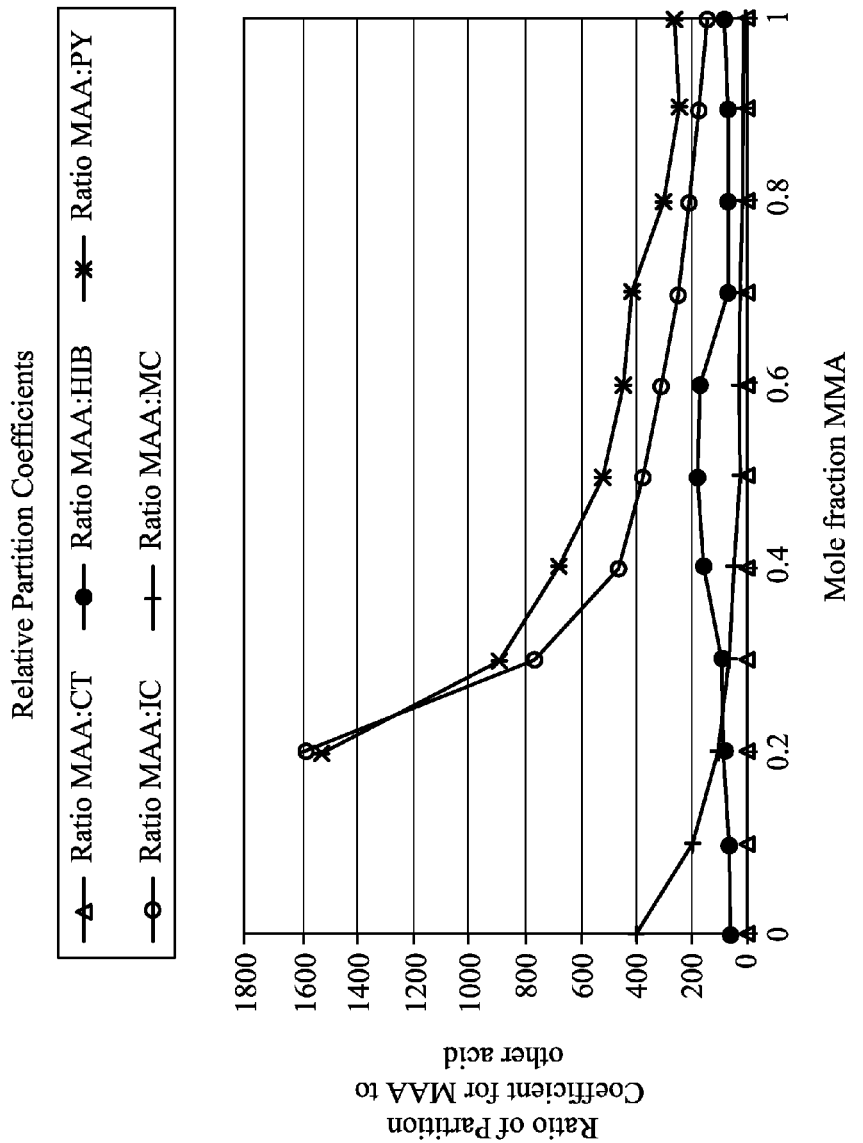
FIG. 3 shows a plot of relative partition coefficient for a range of acids with MMA against MMA fraction in toluene.

The relative partition coefficients may also change with composition. FIG. 3 compares the ratio of Partition Coefficient for MAA with that for each of the other acids.

Thus the comparative examples show that selectivity is higher if pure toluene is used. However use of some MMA allows a higher concentration of MAA to be extracted whilst lowering selectivity.

COMPARATIVE EXAMPLE 5

The extraction of a solution of 0.1M MAA in aqueous solution into an equivalent volume of toluene was determined after addition of 0.05M sodium hydroxide. The amount of MAA transferred fell from 48% to 26%. The results are shown in the first two rows of table 5

EXAMPLES 1-3

Sufficient itaconic acid to give a 0.1M solution was added to the MAA+sodium hydroxide containing aqueous solution of comparative example 5 and the MAA transfer dramatically improved to 44.7% extraction into toluene. The data are shown in table 5. The experiment was repeated with citraconic or mesaconic acids instead of Itaconic acid. Very similar results were obtained.

TABLE 5

| | Concentration of MAA in aqueous solution/M | Added NaOH/M | Added Acid/M | % Transfer into Toluene |
|---|---|---|---|---|
| Comp Ex 1 | 0.1 | | | 48.0 |
| Comp Ex 5 | 0.1 | 0.05 | | 26.0 |
| Ex 1 | 0.1 | 0.05 | Itaconic Acid, 0.1 | 44.7 |
| Ex 2 | 0.1 | 0.05 | Citraconic Acid, 0.1 | 48.1 |
| Ex 3 | 0.1 | 0.05 | Mesaconic Acid, 0.1 | 46.3 |

EXAMPLES 4-30 AND COMPARATIVE EXAMPLES 6-9

0.1M concentrations of various di and tricarboxylic acids added to an aqueous solution of 0.1M MAA containing different levels of NaOH were extracted with an equal volume of toluene.

Figure 4:
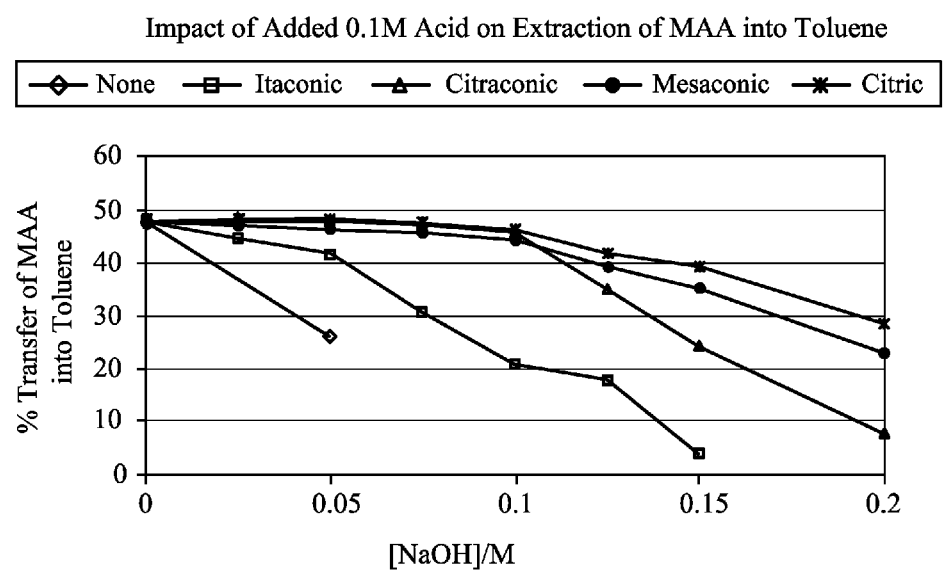
FIG. 4 shows the effect of adding base and dicarboxylic acid on transfer of MAA between aqueous and organic phases.

The quantity of MAA extracted fell much more slowly as sodium hydroxide concentration increased, in the presence of one of the added carboxylic acids than in the absence of added di/tri carboxylic acid. The effect was most marked with citric and mesaconic acids. Table 6 shows the experimental data, which are presented graphically in FIG. 4.

TABLE 6

| | [MAA]/M | [NaOH]/M | Acid | [Acid] | % transfer |
|---|---|---|---|---|---|
| Comp Ex 1 | 0.1 | 0 | None | | 48 |
| Comp Ex 5 | 0.1 | 0.05 | None | | 2 6.04 |
| Comp Ex 6 | 0.1 | 0 | Itaconic | 0.1 | 47.99 |
| Ex 4 | 0.1 | 0.025 | Itaconic | 0.1 | 44.59 |
| Ex 5 | 0.1 | 0.05 | Itaconic | 0.1 | 41.53 |
| Ex 6 | 0.1 | 0.075 | Itaconic | 0.1 | 30.7 |
| Ex 7 | 0.1 | 0.1 | Itaconic | 0.1 | 20.88 |
| Ex 8 | 0.1 | 0.125 | Itaconic | 0.1 | 17.68 |
| Ex 9 | 0.1 | 0.15 | Itaconic | 0.1 | 3.84 |
| Comp ex 7 | 0.1 | 0 | Citraconic | 0.1 | 47.58 |
| Ex 10 | 0.1 | 0.025 | Citraconic | 0.1 | 47.71 |
| Ex 11 | 0.1 | 0.05 | Citraconic | 0.1 | 48.06 |
| Ex 12 | 0.1 | 0.075 | Citraconic | 0.1 | 47.29 |
| Ex 13 | 0.1 | 0.1 | Citraconic | 0.1 | 45.52 |
| Ex 14 | 0.1 | 0.125 | Citraconic | 0.1 | 35.05 |
| Ex 15 | 0.1 | 0.15 | Citraconic | 0.1 | 24.21 |
| Ex 16 | 0.1 | 0.2 | Citraconic | 0.1 | 8.12 |
| Comp Ex 8 | 0.1 | 0 | Mesaconic | 0.1 | 47.36 |
| Ex 17 | 0.1 | 0.025 | Mesaconic | 0.1 | 46.98 |
| Ex 18 | 0.1 | 0.05 | Mesaconic | 0.1 | 46.32 |
| Ex 19 | 0.1 | 0.075 | Mesaconic | 0.1 | 45.66 |
| Ex 20 | 0.1 | 0.1 | Mesaconic | 0.1 | 44.05 |
| Ex 21 | 0.1 | 0.125 | Mesaconic | 0.1 | 39.16 |
| Ex 22 | 0.1 | 0.15 | Mesaconic | 0.1 | 35.15 |
| Ex 23 | 0.1 | 0.2 | Mesaconic | 0.1 | 23 |
| Comp Ex 9 | 0.1 | 0 | Citric | 0.1 | 47.82 |
| Ex 24 | 0.1 | 0.025 | Citric | 0.1 | 48.27 |
| Ex 25 | 0.1 | 0.05 | Citric | 0.1 | 48.12 |
| Ex 26 | 0.1 | 0.075 | Citric | 0.1 | 47.44 |
| Ex 27 | 0.1 | 0.1 | Citric | 0.1 | 46.18 |
| Ex 28 | 0.1 | 0.125 | Citric | 0.1 | 41.83 |
| Ex 29 | 0.1 | 0.15 | Citric | 0.1 | 39.19 |
| Ex 30 | 0.1 | 0.2 | Citric | 0.1 | 28.35 |

EXAMPLES 31-34

Table 7 illustrates the use of higher organic phase to aqueous phase ratios leading to higher degrees of extraction of a solution of 0.3M MAA.

TABLE 7

| | aq:toluene v/v | % transfer |
|---|---|---|
| Ex 31 | 1:1 | 64 |
| Ex 32 | 1:2 | 72 |
| Ex 33 | 1:3 | 76 |
| Ex 34 | 1:4 | 85 |

EXAMPLES 35-39

Table 8 further shows that the use of serial extractions can increase the MAA transfer still further. The starting solution was 0.3M MAA in water.

TABLE 8

| | aq:toluene v/v | % transfer |
|---|---|---|
| | 1:1 vol | |
| Ex 31 | 1:1 | 63.6 |
| | 1:2 vol | |
| Ex 32 | 1:2 | 72.0 |
| Ex 35 | 2 × 1:1 | 80.2 |
| | 1:3 vol | |
| Ex 33 | 1:3 | 75.9 |
| Ex 36 | 1:2 + 1:1 | 84.9 |
| Ex 37 | 3 × 1:1 | 88.1 |
| | 1:4 vol | |
| Ex 34 | 1:4 | 84.9 |
| Ex 38 | 2 × 1:2 | 88.0 |
| Ex 39 | 4 × 1:1 | 92.4 |

EXAMPLE 40

In a further experiment 0.01M citramalic acid decomposition was conducted with reaction flow in order to test the use of toluene extraction during the reaction; in this experiment, the flow of aqueous solution of dicarboxylic acid was mixed with an equal rate of flow of toluene before entering the reactor. Conditions were as follows: 0.01M Citramalic acid (CM) in water with 50 mM NaOH, 2000 psi at variable temperature, with a fixed residence time of 480 seconds. Initial flow consisted of CM and NaOH dissolved in water and toluene in a 50:50 ratio by volume. The yields of products in the two phases detected by HPLC analysis are displayed in table 9. Analysis of the organic phase indicated an absolute MAA yield of 3.42%, with no other products detected. The yield of MAA detected in the aqueous phase was 34.61%, therefore the partition coefficient for MAA between the toluene and aqueous phases=28.5 after cooling to ambient temperature. Thus the solvent may be added to the aqueous phase before the decomposition period as well as after cooling.

TABLE 9

|  | Detected in Aqueous Phase | Detected in Toluene Phase |
| --- | --- | --- |
| Mass Balance | 54.83 | 0.00 |
| Conversion | 93.25 | 0.00 |
| PY | 3.62 | 0.00 |
| CC | 4.53 | 0.00 |
| IC | 0.76 | 0.00 |
| HIB | 3.85 | 0.00 |
| CM | 0.00 | 0.00 |
| MC | 0.71 | 0.00 |
| MAA | 34.61 | 3.42 |

Key:-
IC Itaconic Acid
MC Mesaconic Acid
CC Citraconic Acid
HIB Hydroxyisobutyric Acid
PY Pyruvic Acid

EXAMPLES 41-46 AND COMP EX 10

Solutions of a mixture of dibasic acids and methacrylic acid were prepared in water containing 0.1M of each acid. Sodium hydroxide was added to each solution at a different concentration as shown in table 10. The aqueous solution was extracted with an equal volume of toluene at room temperature. The quantity in the organic and aqueous layers are shown in the table.

TABLE 10

|  | [NaOH] | [MAA] | [CC] | [IC] | [MC] | water [MAA] | toluene [MAA] |
| --- | --- | --- | --- | --- | --- | --- | --- |
| Comp Ex 10 | 0 | 0.1 | 0.1 | 0.1 | 0.1 | 0.052 | 0.048 |
| Ex 41 | 0.025 | 0.1 | 0.1 | 0.1 | 0.1 | 0.048 | 0.052 |
| Ex 42 | 0.05 | 0.1 | 0.1 | 0.1 | 0.1 | 0.050 | 0.050 |
| Ex 43 | 0.075 | 0.1 | 0.1 | 0.1 | 0.1 | 0.052 | 0.048 |
| Ex 44 | 0.1 | 0.1 | 0.1 | 0.1 | 0.1 | 0.051 | 0.049 |
| Ex 45 | 0.125 | 0.1 | 0.1 | 0.1 | 0.1 | 0.050 | 0.050 |
| Ex 46 | 0.15 | 0.1 | 0.1 | 0.1 | 0.1 | 0.051 | 0.049 |

In the presence of 0.3M of combined dicarboxylic acids, the addition of base has no effect on the concentration of MAA extracted. In fact, by comparison with data in example 5, and table 5, it is obvious that the amount extracted was the same as for a solution free of dicarboxylic acid and base. This shows the effectiveness of the presence of the dicarboxylic acid in preventing the loss of organic solvent solubility in the presence of base.

COMPARATIVE EXAMPLE 11

Solutions of acrylic acid in water were extracted with toluene under the same conditions as in comparative example 3 except that the acid was changed from MAA to AA.
The starting concentrations and the quantity extracted into toluene are shown in table 11.

TABLE 11

|  | Conc/M | [organic]/M | [aq]/M |
| --- | --- | --- | --- |
| Comp Ex 11a | 1 | 0.20 | 0.80 |
| Comp Ex 11b | 0.75 | 0.12 | 0.63 |
| Comp Ex 11c | 0.5 | 0.064 | 0.44 |
| Comp Ex 11d | 0.25 | 0.026 | 0.22 |
| Comp Ex 11e | 0.125 | 0.0070 | 0.12 |
| Comp Ex 11f | 0.0625 | 0.0025 | 0.060 |
| Comp Ex 11g | 0.0312 | 0.00098 | 0.030 |
| Comp Ex 11h | 0.0156 | 0.00052 | 0.015 |
| Comp Ex 11j | 0.0078 | 0.00021 | 0.0076 |

Figure 5:
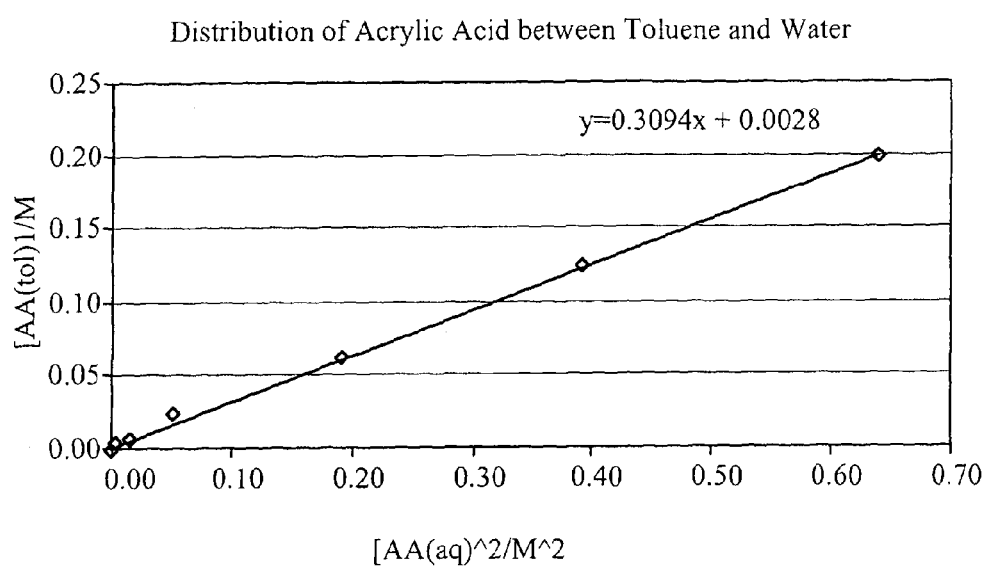
FIG. 5 shows the distribution of acrylic acid between water and toluene.

The relative concentration between the aqueous and organic phases is plotted according to the equation $[AA_{tol}] = K[AA_{aq}]^2$ and shown in FIG. 5.

The excellent straight line fit has a much lower slope than for example 3, indicating that AA much prefers the aqueous layer.

COMPARATIVE EXAMPLE 12

In order to increase the solubility of the AA in the organic layer a higher polarity is likely to be required. The extraction of a 0.1M aq AA solution was studied with an equal volume of a mixture between toluene and butanone.

| % Butanone | % extracted Maleic acid | % extracted Acrylic acid |
| --- | --- | --- |
| 0 | 0 | 5.01 |
| 10 | 0.32 | 14.57 |
| 20 | 1.46 | 25.26 |
| 30 | 3.41 | 35.45 |
| 40 | 5.19 | 44.14 |
| 50 | 10.62 | 53.47 |
| 60 | 10.77 | 57.31 |
| 70 | 15.01 | 63.39 |
| 80 | 19.88 | 67.47 |
| 90 | 27.09 | 70.04 |
| 100 | 34.32 | 65.56 |

There is a very large increase in the extent of extraction as the butanone concentration increases, although the selectivity of extraction falls. It is likely that a mixture containing sodium salts will show a much improved separation between acrylic acid solubility and maleic acid solubility and that an appropriate choice of solvent of intermediate polarity will allow sufficiently effective a separation that the acrylic acid can be further purified by e.g. distillation.

PREPARATIVE EXAMPLES

Experiments Conducted Using the Flow Reaction
Use the Procedure as Outlined Below Flow Reaction Procedure A reactant feed solution was prepared comprising itaconic, citraconic, mesaconic acid or citramalic acid at a concentration of 0.5 M and sodium hydroxide also at a concentration of 0.5 M. The itaconic acid used (>=99%) was obtained from Sigma Aldrich (Catalogue number: L2,920-4); citraconic acid (98+%) was obtained from Alfa Aesar (L044178); mesaconic acid (99%) was obtained from Sigma Aldrich (Catalogue number: 13,104-0). The citramalic acid solution is prepared by dissolving solid (R)-(−)-citramalic acid (commercially available from VWR International) with sodium hydroxide catalyst in nano-pure water to the required concentration.

The deionised water used for solvation of the acids/NaOH was first degassed via sonication in an Ultrasound Bath (30 KHz) for a period of 5 minutes.

This reactant feed solution was fed into the reactor system via a Gilson 305 HPLC pump module fitted with a Gilson 10 SC pump head. The rate at which the reactant feed solution was pumped into the reactor system depended on the residence time required and the volume of the reactor. The feed rate was also dependent on the density of the reaction media which in turn depended on the reaction temperature.

The reactant feed solution was pumped to the reactor via 1/16" internal diameter stainless steel (SS 316) pipe (Sandvik). The reactor consisted of a straight section of 1/2" SS 316 pipe, encased in an aluminium block fitted with two 800 W Watlow heater cartridges. The transition of the SS 316 piping from 1/16" to 1/2" was achieved with Swagelok SS 316 reducing unions and required an intermediate step of 1/8" pipe (i.e. 1/16" pipe to 1/8" pipe to 1/2" pipe).

The volume of the reactor was calculated theoretically, and confirmed from the difference in weight when the reactor was filled with water and when it was dry; for the experiments described, the volume of the reactor was 19.4 cm$^3$. After the 1/2" pipe 'reactor', the piping was reduced back down to 1/16", before meeting a Swagelok SS 316 1/16" cross-piece. At this cross-piece, a thermocouple (type K) was used to monitor the temperature of the exit feed.

Reactor volume (used for residence time) is defined as the volume of the 1/2" section of pipe between the two 1/2" to 1/8" reducers located immediately before and after the aluminium block.

The product mixture is finally passed through a heat exchanger (a length of 1/8" pipe within a 1/4" pipe through which cold water was passed in contra flow) and a manual Tescom Back-Pressure Regulator through which back-pressure (pressure throughout the whole system between this point and the pump head) was generated: the pressure employed was 3000 psi for all experiments described. Samples were collected in vials before being prepared for analysis.

The required temperature for reaction was achieved using a thermostat fitted with a Gefran controller (800 P), which mediated power applied to the two Watlow cartridge heaters. Each set of experiments involved working at a single temperature while varying residence time between runs. The required flow rate for the first run was set at the Gilson pump module. The pump was then left for a period of around 20 minutes, pumping only deionised water, in order for the heat-transfer between the aluminium block to have become consistent. The heat-transfer was deemed to have achieved equilibrium when the temperature indicated by the thermocouple located at the reactor exit feed position did not change (accurate to 1° C.) for a period of more than 5 minutes. At this stage the inlet of the pump was transferred from the container of deionised water to the container of the prepared reactant mixture. The total volume of the apparatus (including reactor) was approximately double that of the reactor itself; this was previously determined experimentally. For a particular flow rate, the reactant mixture was left pumping for approximately three times the required period for it to have begun emerging from the final outlet, in order to ensure that a steady-state of reaction had been achieved. After this time a 20 ml sample of the apparatus exit solution was collected for analysis. Both the rate of collection of the exit solution and the rate at which the reaction solution was consumed were recorded against time in order to monitor the consistency of the pump efficiency. Following sample collection from a particular run, the pump inlet was switched back to the container of deionised water, and the flow rate was increased to its maximum for a period of approximately 10 minutes to ensure that all remaining material from the previous run had been purged from the system. This procedure was then repeated for the subsequent residence time to be investigated.

Analysis

Quantitative analysis of products was achieved using an Agilent 1200 series HPLC system equipped with a multi wave-length UV detector. Products were separated using a Phenomenex Rezex RHM monosaccharide H$^+$ (8%) column held at 75° C., protected by a guard column. The method used was isocratic, implementing a 0.4 mlmin$^{-1}$ flow rate of aqueous 0.005 M H$_2$SO$_4$ mobile phase. The compounds contained in product samples were found to have optimum UV absorbance at the shortest wavelength capable of the MWD detector of 210 nm (bandwidth 15 nm). All product compounds were calibrated for their UV detection, by correlating their UV absorbance against a range of concentrations. Linear response ranges were determined for each compound, and the most compatible range of concentrations found for all compounds of interest was between $5\times10^{-3}$ M and $1\times10^{-3}$ M. Thus, adequate quantitative detection of most products was achieved with a 1 to 100 dilution of samples obtained from the apparatus before HPLC analysis (a dilution of 1 to 100 would mean that when starting with a 0.5 M reaction solution, any product generated in a yield of between 20% -100% would fall within the linear response range of concentrations). Where compounds fell outside this linear response range (e.g. a yield of less than 20%), a second HPLC analysis was conducted using a dilution of 1 to 10. Any samples which were not accurately quantified using the 1 to 10 dilution method were considered to be trace in concentration and therefore negligible.

Procedure

The following procedure was carried out. The reagent mixture comprising acid and sodium hydroxide was first prepared. The required flow rate to achieve the residence time was calculated using the reactor volume and the density of water (calculated from temperature).

Figure 6:
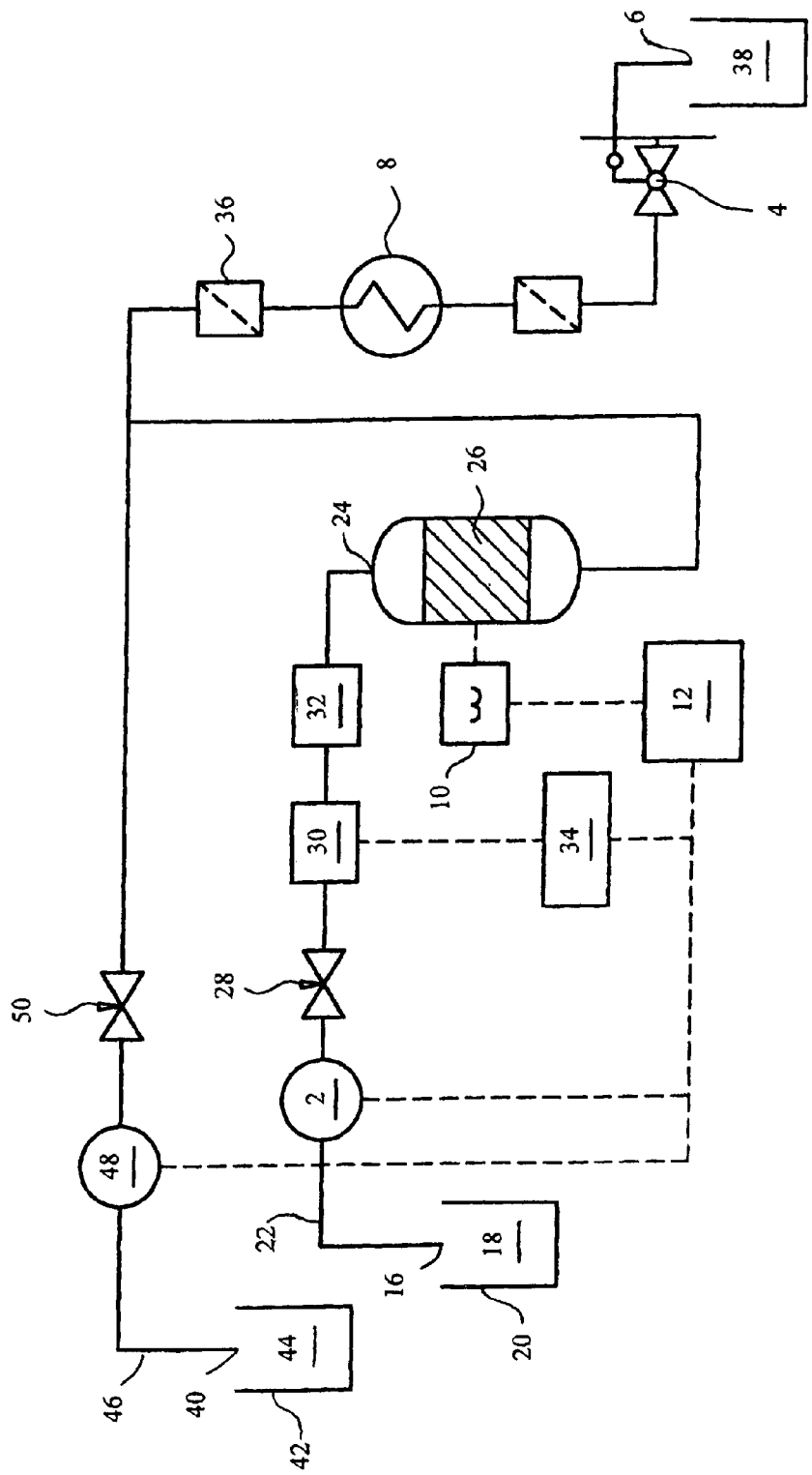
FIG. 6 shows a schematic view of suitable apparatus for the base catalysed decomposition of dicarboxylic acids.

FIG. 6 shows a schematic representation of the apparatus for the present invention. Reaction solution 18 was located in receptacle 20 which was connected to inlet 16.

The inlet was connected via conduit 22 to the reactant pump 2 which was operable to pump the solution 18 to the reactor tube 24 tube which was housed in a heater cartridge 26 which extended circumferentially along the reactor 24 length. The conduit 22 between the pump 2 and the reactor 24 proceeded from the pump via a valve 28 for operation control, pressure monitor 30 and pressure relief valve 32. In addition, a trip switch 34 was connected to the pressure monitor 30, reactant pump 2 and a temperature monitor 14. The temperature monitor 14 was located in conduit 22 immediately after reactor 24 and before outlet 6. In addition, after the monitor 14, the conduit proceeded to the outlet via a filter 36, heat exchanger 8 and back pressure regulator 4. At the outlet 6, the product was collected in collection receptacle 38.

The reactor 24 also included a temperature control unit 10, 12 to control the temperature of the reactor 24. The apparatus also included a quenching system which includes a separate inlet 40 for quench water 44 in quench water receptacle 42. The inlet 40 was connected to the outlet 6 via conduit 46 which included a separate quench pump 48 followed by a valve 50 for control of the quench water. The quench water conduit 46 met the reaction conduit 22 immediately after the temperature monitor 14 of the reactor 24 and before filter 36 to quench any reaction after the reactor. The quench pump 48 and temperature controller unit 10, 12 were also connected to trip switch 34 for necessary shut down when the trip criteria are met.

The reactant pump 2 was turned on and deionised water was pumped into the system. The back pressure regulator 4 was gradually adjusted to the required pressure (3000 psi).

The pump operation efficiency was checked at 5 ml min$^{-1}$ by recording time taken to collect a volume of 20 ml of water from system outlet 6. >90% efficiency was acceptable.

The pump flow rate is then set to that required for the run.

The water supply (not shown) to the heat exchanger 8 was set to a low-moderate flow, depending on the reaction temperature and pump flow rate for the experiment.

The heater thermostat 10 fitted with a temperature controller 12 was set to the required temperature for the run.

Once the required temperature had been reached (as indicated by thermostat 10), reactor outlet temperature was monitored by the reactor temperature monitor 14 until the value (accurate to 1° C.) was observed to remain static for a period of at least 5 minutes (this usually took approximately 20 minutes).

The pump inlet 16 was switched from the deionised water container (not shown) to the prepared reagent mixture container 18 (this requires stopping the pump flow for a few seconds). The initial volume of reagent mixture in container 18 was recorded.

Calculations can indicate the period before product solution will begin to emerge from the system outlet 6. However, in practice, this was confirmed by the visual and audible presence of gas bubbles exiting the apparatus (generated from the decomposition of reagents). This was allowed to continue for a period that is ×3 the period taken for the product solution to emerge. This ensured that the product mixture is homogenous.

At the outlet 6, 20 ml of product solution was collected and the time taken for this collection was recorded. A final time and volume reading was also taken for the reagent mixture.

After product collection, the pump inlet was transferred back to the deionised water container, and the pump was set to "prime mode" (maximum flow rate) and left for a period of approximately 10 minutes.

The flow rate of the pump was then set to the required value for the subsequent run.

Again the reactor outlet temperature was monitored and was considered steady when the value did not change for a period of at least 5 minutes (this usually took approximately 10 minutes).

This experimental method was repeated until all required runs for the experiment had been performed.

After all runs had been completed, the deionised water was pumped into the system with the pump on prime mode and the heater (thermostat) was switched off.

When the reactor outlet temperature had dropped below 80° C., the pump was switched off and the water supply to the heat exchanger was also ceased.

Methacrylic Acid Extraction

Solutions prepared according to the preparative procedure above were extracted with an equal volume of toluene. In the first set of experiments no extra acid was added. In the second set the acid used for the original high temperature decomposition was added such that the total concentration of dicarboxylic acids (Itaconic, citraconic, mesaconic, Citramalic) plus 2-hydroxyisobutyric acid equalled 0.5M, which was the starting concentration for the original decomposition. The results in table 10 show that addition of acid has a very large impact on the amount extracted at the high concentrations of base present.

TABLE 10

| | Example 47 | Example 48 | Example 49 | Example 50 | Example 51 | Example 52 | Example 53 |
|---|---|---|---|---|---|---|---|
| Feed | IC | IC | IC | IC | IC | MC | CC |
| Original Feed conc/M | 0.5 | 0.5 | 0.5 | 0.5 | 0.5 | 0.5 | 0.5 |
| MAA | 19.25% | 64.73% | 58.36% | 56.74% | 54.42% | 44.89% | 44.93% |
| ICA | 16.35% | 0.99% | 0.84% | 0.00% | 0.16% | 7.72% | 5.88% |
| Citramalic | 0.00% | 0.00% | 0.00% | 0.00% | 0.00% | 0.00% | 0.00% |
| CCA | 36.76% | 1.69% | 0.50% | 0.00% | 0.26% | 16.27% | 12.40% |
| MCA | 15.18% | 2.08% | 0.64% | 0.08% | 0.30% | 13.28% | 9.93% |
| HIB | 11.26% | 23.04% | 22.12% | 19.33% | 13.07% | 13.72% | 14.25% |
| PY | 0.36% | 3.06% | 2.69% | 2.63% | 2.67% | 1.31% | 1.77% |
| CT | 0.07% | 0.91% | 0.74% | 0.53% | 0.63% | 0.63% | 0.65% |
| Acids Mass Balance | 99.23% | 96.50% | 85.89% | 79.31% | 71.51% | 97.82% | 89.81% |
| | No added Acid | | | | | | |
| % Extracted | 11.55% | 0.05% | 1.00% | 0.00% | 0.00% | 7.02% | 2.01% |
| pH | 4.87 | 6.65 | >7 | >8 | >8 | 5.34 | 5.70 |
| | Acid Added | | | | | | |
| % Extracted | 20.21% | 29.43% | 28.31% | 28.04% | 27.90% | 30.56% | 29.74% |
| pH | 4.39 | 4.45 | 4.47 | 4.47 | 4.46 | 4.05 | 4.16 |

COMPARATIVE EXAMPLE 12

The efficiency of MAA extraction into a mixture of 2-butanone and o-xylene in the ratio 75:25 was studied. The presence of xylene in this organic mixture partly restricts the solubility of butanone in the aqueous phase, which is a significant issue where butanone is used alone as the organic phase; at this particular ratio, the distribution coefficient for MAA is reported to be a maximum of approximately $K=7.00$.[23] In this case it was found that roughly 80% of MAA was extracted into the organic phase, which appeared extremely desirable; however, other dicarboxylic acids concerned in the decomposition experiments (i.e. IC, CC etc.) also showed a slight affinity to the organic phase of up to 11%.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A method of extracting (meth)acrylic acid from an aqueous reaction medium, the aqueous reaction medium being formed from at least one base catalyst and at least one dicarboxylic acid selected from maleic, fumaric, malic, itaconic, citraconic, mesaconic, and citramalic acid or mixtures thereof in aqueous solution and containing the base catalysed decarboxylation products thereof including (meth)acrylic acid and/or (meth)acrylate base salt, the method comprising the steps of introducing an organic solvent to the said aqueous reaction medium for solvent extraction of the (meth)acrylic acid into an organic phase wherein the method is characterised in that there is added an additional amount of at least one of the said dicarboxylic acids and/or a pre-cursor thereof to the said aqueous reaction medium to enhance the solvent extraction of the (meth)acrylic acid into the organic solvent.

2. A method according to claim 1, wherein the concentration of (meth)acrylic acid in the aqueous phase extraction is at least 0.05 mol dm$^{-3}$.

3. A method according to claim 1, wherein the molar level of base catalyst to the said at least one dicarboxylic acid and/or pre-cursor thereof is maintained at a sub-stoichiometric level in relation to the formation of the first acid salt thereof during the extraction process and the amount of dicarboxylic acid added is determined accordingly.

4. A method according to claim 1, wherein the dicarboxylic acid and/or a pre-cursor thereof is selected from citric, itaconic, citramalic, citraconic and mesaconic acid or mixtures thereof, more preferably, citric, itaconic, citramalic and citraconic acid or mixtures thereof.

5. A method according to claim 1, wherein the dicarboxylic acid is selected from maleic, fumaric, and malic acid or mixtures thereof, more preferably, malic acid or mixtures thereof.

6. A method of extracting (meth)acrylic acid from an aqueous reaction medium, the aqueous reaction medium being formed from at least one base catalyst and at least one dicarboxylic acid selected from fumaric, maleic, malic, itaconic, citraconic, mesaconic or citramalic acid or mixtures thereof in aqueous solution and containing the base catalysed decarboxylation products thereof including (meth)acrylic acid or (meth)acrylate base salt, the method comprising the steps of introducing an organic solvent to the aqueous reaction medium for solvent extraction of the (meth)acrylic acid into the organic phase characterised in that the level of base catalyst to the said at least one dicarboxylic acid and/or pre-cursor thereof is maintained at a sub-stoichiometric level in relation to the formation of the first acid salt thereof during the extraction process.

7. A method according to claim 1, wherein in the case of the (meth)acrylic acid being methacrylic acid, the organic solvent is an external organic solvent with respect to the reaction medium.

8. A method according to claim 1, wherein the dicarboxylic acid is selected from citramalic or itaconic acid.

9. A process for the production of (meth)acrylic acid comprising the steps of:
   forming an aqueous medium of at least one base catalyst and at least one dicarboxylic acid selected from fumaric, maleic, malic, itaconic, citraconic, mesaconic or citramalic acid or mixtures thereof;
   decarboxylating the at least one dicarboxylic acid in the presence of the at least one base catalyst under suitable conditions of temperature and pressure to produce (meth)acrylic acid and/or base salts thereof in the aqueous medium;
   introducing an organic solvent to the said aqueous medium for solvent extraction of the (meth)acrylic acid into an organic phase;
   characterised by the step of adding an additional amount of at least one of the said dicarboxylic acids and/or a pre-cursor thereof to the said aqueous medium to enhance the solvent extraction of the (meth)acrylic acid into the organic solvent.

10. A method or process according to claim 1, wherein the organic solvents for (meth)acrylic acid extraction include hydrocarbon solvents or oxygenated solvents, particularly $C_4$-$C_{20}$ hydrocarbon solvents.

11. A method or process according to claim 10, wherein the solvents include toluene, benzene, ethylbenzene, xylene, trimethylbenzene, octane, heptane, hexane, pentane, cyclopentane, cyclohexane, cycloheptane, cyclooctane, cyclohexene, methylcyclohexane, methylethylketone, methyl methacrylate or mixtures thereof; or ionic liquids which are immiscible with water.

12. A method or process according to claim 10, wherein the mixture of solvents for the extraction of MAA is a $C_4$-$C_{20}$ hydrocarbon solvent and MMA.

13. A method of extracting (meth)acrylic acid from an aqueous reaction medium into an organic phase in contact therewith, the aqueous reaction medium being formed from at least one base catalyst and at least one dicarboxylic acid selected from fumaric, maleic, malic, itaconic, citraconic, mesaconic or citramalic acid or mixtures thereof in aqueous solution and containing the base catalysed decarboxylation products thereof including (meth)acrylic acid or (meth)acrylate base salt and the organic phase comprises a suitable organic solvent for the said (meth)acrylic acid characterised in that in the aqueous reaction medium the relative level of base catalyst to the said at least one dicarboxylic acid and/or pre-cursor thereof is maintained at a sub-stoichiometric level in relation to the formation of the first acid salt thereof during at least part of the extraction.

14. A method of extracting (meth)acrylic acid from an aqueous reaction medium, the aqueous reaction medium being formed from at least one base catalyst and at least one dicarboxylic acid selected from maleic, fumaric, malic, itaconic, citraconic, mesaconic or citramalic acid or mixtures thereof in aqueous solution and containing the base catalysed decarboxylation products thereof including (meth)acrylic acid and/or (meth)acrylate base salt, the method comprising the step of solvent extraction of the (meth)acrylic acid into an organic phase comprising an organic solvent in contact with the said aqueous reaction medium wherein the method is characterised in that there is added an additional amount of at least one of the said dicarboxylic acids and/or a pre-cursor thereof to the said aqueous reaction medium containing the said base catalysed decarboxylation products thereof to enhance the solvent extraction of the (meth)acrylic acid into the organic phase.

15. A method or process according to claim 1, including the step of separating the organic phase from the aqueous phase after extraction followed by subsequent treatment of the organic phase to isolate the (meth)acrylic acid extracted in the extraction process from the organic solvent.

16. A method or process according to claim 1, wherein the organic solvent is introduced to the aqueous medium before or after decarboxylation.

17. A method or process according to claim 1, wherein the sub-stoichiometric level of base is maintained, after, if necessary, being implemented post reaction, during at least that part of the extraction process which is carried out after the decarboxylation step.

18. A method or process according to claim 1, wherein the sub-stoichiometric level of base is maintained throughout the reaction and extraction.

* * * * *

UNITED STATES PATENT AND TRADEMARK OFFICE
CERTIFICATE OF CORRECTION

PATENT NO. : 9,216,938 B2  Page 1 of 1
APPLICATION NO. : 13/984473
DATED : December 22, 2015
INVENTOR(S) : David William Johnson et al.

It is certified that error appears in the above-identified patent and that said Letters Patent is hereby corrected as shown below:

On the Title Page, Item (54) and in the Specification, Column 1, Title

PROCESS FOR THE PRODUCTION OF (METH)ACRYLIC ACID AND DERIVATIVES AND POLYMERS PRODUCED THEREFROM

Signed and Sealed this
Fifth Day of April, 2016

Michelle K. Lee
*Director of the United States Patent and Trademark Office*